US008670842B1

(12) United States Patent
Bornzin et al.

(10) Patent No.: US 8,670,842 B1
(45) Date of Patent: Mar. 11, 2014

(54) INTRA-CARDIAC IMPLANTABLE MEDICAL DEVICE

(71) Applicant: Pacesetter, Inc., Sylmar, CA (US)

(72) Inventors: Gene A. Bornzin, Simi Valley, CA (US); John W. Poore, South Pasadena, CA (US); Zoltan Somogyi, Simi Valley, CA (US); Xiaoyi Min, Camarillo, CA (US); Didier Theret, Porter Ranch, CA (US); Elaine Karaelias, Brea, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/715,732

(22) Filed: Dec. 14, 2012

(51) Int. Cl.
*A61N 1/00* (2006.01)

(52) U.S. Cl.
USPC .......................................................... 607/125

(58) Field of Classification Search
USPC .......................................................... 607/125
See application file for complete search history.

(56) References Cited

U.S. PATENT DOCUMENTS

| 3,835,864 | A | 9/1974 | Rasor et al. |
|---|---|---|---|
| 3,835,869 | A | 9/1974 | Newman et al. |
| 3,943,936 | A | 3/1976 | Rasor et al. |
| 4,278,093 | A | 7/1981 | Lafortune et al. |
| 4,987,897 | A | 1/1991 | Funke |
| 5,193,540 | A | 3/1993 | Schulman et al. |
| 5,358,514 | A | 10/1994 | Schulman et al. |
| 5,405,367 | A | 4/1995 | Schulman et al. |
| 5,411,535 | A | 5/1995 | Fujii et al. |
| 5,487,758 | A | 1/1996 | Hoegnelid et al. |
| 5,545,201 | A | 8/1996 | Helland et al. |

(Continued)

FOREIGN PATENT DOCUMENTS

| EP | 1844812 A1 | 10/2007 |
|---|---|---|
| WO | 2005092431 A1 | 10/2005 |

(Continued)

OTHER PUBLICATIONS

Asirvatham, Samuel J. MD et al., "Intramyocardial Pacing and Sensing for the Enhancement of Cardiac Stimulation and Sensing Specificity," PACE. 2007:30:748-754.

(Continued)

*Primary Examiner* — Robert N Wieland

(57) ABSTRACT

An intra-cardiac implantable medical device (IIMD) system may include a housing and an intra-cardiac (IC) device extension. The housing may be configured to be implanted entirely within a local chamber of the heart. The housing includes a base configured to be secured to the local chamber. The IC device extension may include a proximal end, a distal end, and an extension body extending there between. The proximal end may be coupled to the housing and configured to be located in the local chamber. The extension body may include an IE orientation segment connected to a chamber transition segment that is sufficient in length to extend from the local chamber into an adjacent chamber. The IE orientation segment is configured to be lodged within the adjacent chamber in order to stabilize the system within heart.

25 Claims, 17 Drawing Sheets

(56) References Cited

U.S. PATENT DOCUMENTS

| | | | |
|---|---|---|---|
| 5,679,022 | A | 10/1997 | Cappa et al. |
| 5,814,089 | A | 9/1998 | Stokes et al. |
| 6,141,588 | A | 10/2000 | Cox et al. |
| 6,164,284 | A | 12/2000 | Schulman et al. |
| 6,181,965 | B1 | 1/2001 | Loeb et al. |
| 6,185,452 | B1 | 2/2001 | Schulman et al. |
| 6,208,894 | B1 | 3/2001 | Schulman et al. |
| 6,434,428 | B1 | 8/2002 | Sloman et al. |
| 6,754,536 | B2 | 6/2004 | Swoyer et al. |
| 7,037,311 | B2 | 5/2006 | Parkinson et al. |
| 7,047,076 | B1 | 5/2006 | Li et al. |
| 7,082,336 | B2 | 7/2006 | Ransbury et al. |
| 7,114,502 | B2 | 10/2006 | Schulman et al. |
| 7,363,087 | B2 | 4/2008 | Nghiem et al. |
| 7,383,091 | B1 | 6/2008 | Chitre et al. |
| 7,513,257 | B2 | 4/2009 | Schulman et al. |
| 7,565,195 | B1 | 7/2009 | Kroll et al. |
| 7,634,313 | B1 | 12/2009 | Kroll et al. |
| 7,643,872 | B2 | 1/2010 | Min et al. |
| 7,801,626 | B2 | 9/2010 | Moser |
| 7,860,570 | B2 | 12/2010 | Whitehurst et al. |
| 7,894,915 | B1 | 2/2011 | Chitre et al. |
| 7,899,555 | B2 | 3/2011 | Morgan et al. |
| 7,937,148 | B2 | 5/2011 | Jacobson |
| 7,945,333 | B2 | 5/2011 | Jacobson |
| 8,010,209 | B2 | 8/2011 | Jacobson |
| 8,032,219 | B2 | 10/2011 | Neumann et al. |
| 2004/0015204 | A1 | 1/2004 | Whitehurst et al. |
| 2004/0015205 | A1 | 1/2004 | Whitehurst et al. |
| 2004/0147973 | A1* | 7/2004 | Hauser ............... 607/36 |
| 2006/0009831 | A1 | 1/2006 | Lau et al. |
| 2006/0135999 | A1 | 6/2006 | Bodner et al. |
| 2007/0055310 | A1 | 3/2007 | Lau |
| 2007/0088396 | A1 | 4/2007 | Jacobson |
| 2007/0088400 | A1 | 4/2007 | Jacobson |
| 2008/0097566 | A1 | 4/2008 | Colliou |
| 2008/0255647 | A1 | 10/2008 | Jensen et al. |
| 2009/0082828 | A1 | 3/2009 | Ostroff |
| 2009/0299433 | A1 | 12/2009 | Dingman et al. |
| 2010/0010381 | A1 | 1/2010 | Skelton et al. |
| 2010/0198288 | A1 | 8/2010 | Ostroff |
| 2011/0071586 | A1 | 3/2011 | Jacobson |
| 2011/0077708 | A1 | 3/2011 | Ostroff |
| 2011/0208260 | A1 | 8/2011 | Jacobson |
| 2011/0218587 | A1 | 9/2011 | Jacobson |
| 2011/0238077 | A1 | 9/2011 | Wenger |
| 2011/0251660 | A1 | 10/2011 | Griswold |
| 2011/0251662 | A1 | 10/2011 | Griswold et al. |

FOREIGN PATENT DOCUMENTS

| | | |
|---|---|---|
| WO | 2007047681 A2 | 4/2007 |
| WO | 2007047681 A3 | 9/2008 |
| WO | 2009039400 A1 | 3/2009 |
| WO | 2009078751 A1 | 6/2009 |
| WO | 2010088687 A1 | 8/2010 |

OTHER PUBLICATIONS

Brinker, Jeffrey A., "Endocardial Pacing Leads: The Good, the Bad, and the Ugly," PACE. 1995;18(Pt 1):953-954.

Calvagna, Giuseppe M. et al., "A complication of pacemaker lead extraction: pulmonary embolization of an electrode fragment," Europace. 2010;12:613.

Da Costa, Sergio Sidney Do Carmo et al., "Incidence and Risk Factors of Upper Extremity Deep Vein Lesions After Permanent Transvenous Pacemaker Implant: A 6-Month Follow-up Prospective Study," PACE. 2002;25:1301-1306.

Hauser, Robert G. et al., "Deaths and cardiovascular injuries due to device-assisted implantable cardioverter-defibrillator and pacemaker lead extraction," Europace. 2010;12:395-401.

Heaven, D.J. et al., "Pacemaker lead related tricuspid stenosis: a report of two cases," Heart. 2000;83:351-352.

Henz, Benhur D. MD et al., "Synchronous Ventricular Pacing without Crossing thetricuspid Valve or Entering the Coronary Sinus—Preliminary Results," J Cardiovasc Electrophysiol. 2009(Dec.);20:1391-1397.

Hesselson, Aaron B. Bsee et al., "Deleterious Effects of Long-Term Single-chamber Ventricular Pacing in Patients With Sick Sinus Syndrome: The Hidden Benefits of dual-Chamber Pacing," J Am Coll Cardiol. 1992;19:1542-1549.

Klug, Didier MD et al., "Systemic Infection Related to Endocardities on Pacemaker Leads—Clinical Presentation and Management," Circulation. 1997;95:2098-2107.

Korkeila, Petri et al., "Clinical and laboratory risk factors of thrombotic complications after pacemaker implantation: a prospective study," Europace. 2010;12:817-824.

Marrie, Thomas J. MD et al., "A Scanning and Transmission Electron Microscopic Study of an Infected Endocardial Pacmaker Lead," Circulation. 1982;66(6):1339-1341.

Menozzi, Carlo et al., "Intrapatient Comparison Between Chronic VVIR and DDD pacing in Patients Affected by High Degree AV Block Without Heart Failure," PACE. 1990(Dec-Pt II);13:1816-1822.

Stellbrink, Christoph et al.,"Technical considerations in implanting left ventricular pacing leads for cardiac resynchronization therapy," European Heart Journal Supplements. 2004;6(Supp D):D43-D46.

Spickler, J. William PhD, "Totally Self-Contained Intracardiac Pacemaker," J Electrocardiology. 1970;3(3-4):325-331.

Van Rooden, Cornelis J. MD et al., "Incidence and Risk Factors of Early Venous Thrombosis Associated with Permanent Pacemaker Leads," J Cardiovasc Electrophysiol. 2004(Nov.);15:1258-1262.

Vardas, P.E. et al., "A Miniature Pacemaker Introduced Intravenously and Implanted Endocardially. Preliminary Findings from an Experimental Study," Eur J Card Pacing Electrophysiol. 1991;1:27-30.

Voet, J.G. et al., "Pacemaker lead infection: report of three cases and review of the literature," Heart. 1999;81:88-91.

Walters, M.I. et al., "Pulmonary Embolization of a Pacing Electrode Fragment Complicating Lead Extraction," PACE. 1999;22:823-824.

* cited by examiner

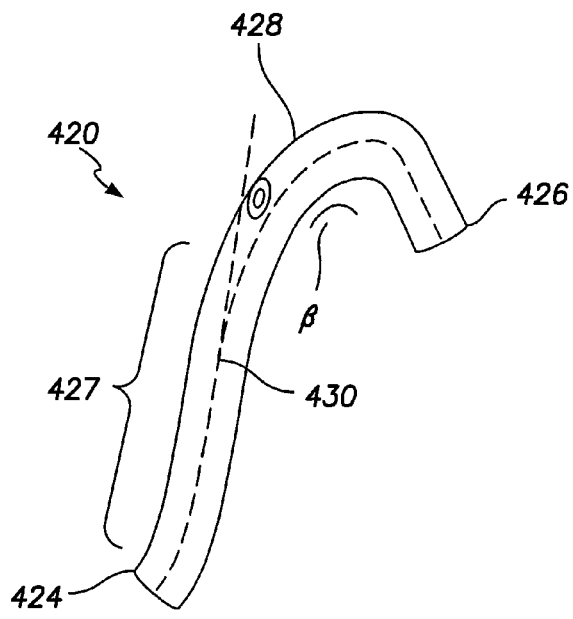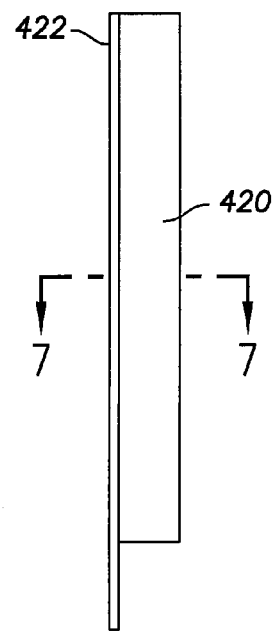
FIG. 5　　　　　　　　FIG. 6
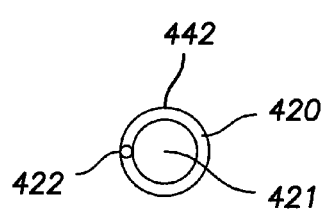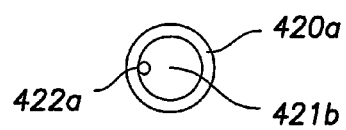
FIG. 7　　　　　　　　FIG. 8

INTRA-CARDIAC IMPLANTABLE MEDICAL DEVICE

FIELD

Embodiments of the present disclosure generally relate to an intra-cardiac system and method, and, more particularly, to a system and method of implanting a system entirely within a heart of a patient.

BACKGROUND

Numerous medical devices exist today, including but not limited to electrocardiographs ("ECGs"), electroencephalographs ("EEGs"), squid magnetometers, implantable pacemakers, implantable cardioverter-defibrillators ("ICDs"), neurostimulators, electrophysiology ("EP") mapping and radio frequency ("RF") ablation systems, and the like (hereafter generally "implantable medical devices" or "IMDs"). IMDs commonly employ one or more leads with electrodes that either receive or deliver voltage, current or other electromagnetic pulses (generally "energy") from or to an organ or tissue (collectively hereafter "tissue") for diagnostic or therapeutic purposes.

Typically, an IMD is outside of the heart. To sense atrial cardiac signals and to provide right atrial chamber stimulation therapy, the IMD is coupled to an implantable right atrial lead including at least one atrial tip electrode that typically is implanted in the patient's right atrial appendage. The right atrial lead may also include an atrial ring electrode to allow bipolar stimulation or sensing in combination with the atrial tip electrode.

To sense the left atrial and left ventricular cardiac signals and to provide left-chamber stimulation therapy, the IMD is coupled to the "coronary sinus" lead designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead is designed to: receive atrial and/or ventricular cardiac signals; deliver left ventricular pacing therapy using at least one left ventricular tip electrode for unipolar configurations or in combination with left ventricular ring electrode for bipolar configurations; deliver left atrial pacing therapy using at least one left atrial ring electrode as well as shocking therapy using at least one left atrial coil electrode.

The IMD may also be in electrical communication with the patient's heart by way of the implantable right ventricular lead including a right ventricular (RV) tip electrode, a right ventricular ring electrode, a right ventricular coil electrode, a superior vena cava (SVC) coil electrode, and so on. Typically, the right ventricular lead is inserted transvenously into the heart so as to place the right ventricular tip electrode in the right ventricular apex such that the RV coil electrode is positioned in the right ventricle and the SVC coil electrode will be positioned in the right atrium and/or superior vena cava. Accordingly, the right ventricular lead is capable of receiving cardiac signals, and delivering stimulation in the form of pacing and shock therapy to the right ventricle.

Notably, a substantial portion of the leads, as well as the IMD itself are outside of the patient's heart. Consequently, bacteria and the like may be introduced into the patient's heart through the leads, as well as the IMD, thereby increasing the risk of infection within the heart.

Additionally, because the IMD is outside of the heart, the patient may be susceptible to Twiddler's syndrome, which is a condition caused by the shape and weight of the IMD itself. Twiddler's syndrome is typically characterized by a subconscious, inadvertent, or deliberate rotation of the IMD within the subcutaneous pocket formed in the patient. In one example, a lead may retract and begin to wrap around the IMD. Also, one of the leads may dislodge from the endocardium and cause the IMD to malfunction. Further, in another typical symptom of Twiddler's syndrome, the IMD may stimulate the diaphragm, vagus, or phrenic nerve, pectoral muscles, or brachial plexus. Overall, Twiddler's syndrome may result in sudden cardiac arrest due to conduction disturbances related to the IMD.

Further, locating the IMD outside of the heart may cause discomfort to the patient, erode skin proximate the IMD in its subcutaneous pocket, and the like. As such, permanently-implanted pacemakers (PPMs) designed to be wholly contained within the heart have been developed.

Currently, permanently-implanted pacemakers (PPMs) utilize one or more electrically-conductive leads (which traverse blood vessels and heart chambers) in order to connect a canister with electronics and a power source (the can) to electrodes affixed to the heart for the purpose of electrically exciting cardiac tissue (pacing) and measuring myocardial electrical activity (sensing). The leads may experience certain limitations, such as incidences of venous stenosis or thrombosis, device-related endocarditis, lead perforation of the tricuspid valve and concomitant tricuspid stenosis; and lacerations of the right atrium, superior vena cava, and innominate vein or pulmonary embolization of electrode fragments during lead extraction.

A small sized PPM device has been proposed, termed a leadless pacemaker (LLPM), that is characterized by the following features: electrodes are affixed directly to the CAN of the device; the entire device is attached to the heart; and the LLPM is capable of pacing and sensing in the chamber of the heart where it is implanted.

As an example, an intra-cardiac pacemaker has been developed that is implanted and contained within a heart of a patient. Often, intra-cardiac IMDs are delivered into a right atrium of the heart through the superior vena cava. The IMD is maneuvered to an implantation location, such as a right atrial appendage, ventricular vestibule, or the like, with a tool. However, many physicians prefer to deliver an IMD into the heart through the inferior vena cava. Yet, many of the tools and methods configured for superior vena cava delivery are not well-suited for inferior vena cava delivery. Moreover, many tools configured for inferior cava delivery are expensive. Indeed, some tools designed for inferior cava delivery approach the cost of the IMDs themselves. Further, known methods for inferior vena cava delivery are often difficult to perform.

SUMMARY

Certain embodiments of the present disclosure provide an intra-cardiac implantable medical device (IIMD) system that includes a housing and an intra-cardiac (IC) device extension. The housing may be configured to be implanted entirely within a local chamber of the heart. The housing includes a base configured to be secured to the local chamber. The IC device extension includes a proximal end, a distal end, and an extension body extending therebetween. The proximal end is coupled to the housing and configured to be located in the local chamber. The extension body includes an IIMD-to-electrode (IE) orientation segment connected to a chamber transition segment that is sufficient in length to extend from the local chamber into an adjacent chamber proximate an inferior vena cava. At least a portion of the IE orientation segment is configured to be lodged within the adjacent chamber proximate the inferior vena cava in order to stabilize the system within heart.

The housing may be configured to be securely anchored within the local chamber. The IC device extension may be configured to be securely lodged between wall portions of the adjacent chamber.

The IE orientation segment may include a right atrial appendage (RAA) stabilization segment connected to an inferior vena cava (IVC) stabilization segment through a spanning segment. The RAA stabilization segment may be configured to be proximate an RAA of the heart and the IVC stabilization segment may be configured to be proximate the inferior vena cava of the heart. The RAA stabilization segment may include an RAA fixation mechanism having at least one electrode configured to abut into a portion of the RAA. The RAA stabilization segment may include an active interim segment extending therefrom. Each of the RAA stabilization segment and the IVC stabilization segment may include at least one arcuate turn. The RAA stabilization segment may include the distal end configured to abut into the RAA. The IVC stabilization segment may include an arcuate curved segment configured to abut into a wall portion of the right atrium opposite the RAA. The distal end may be formed into a loop.

Certain embodiments of the present disclosure provide an intra-cardiac implantation system that may include an implantable medical device configured to be implanted into a heart. The IIMD may include a housing configured to be implanted entirely within a local chamber of the heart, and an intra-cardiac device extension having an extension proximal end, an extension distal end, and an extension body extending there between. The IIMD may also include an extension body including an IIMD-to-electrode orientation segment connected to a chamber transition segment that is sufficient in length to extend from the local chamber into an adjacent chamber.

The system may also include an introducer assembly configured to implant the IIMD into the heart. The introducer assembly may include a sheath having a sheath proximal end and a sheath distal end. An internal passage is defined between the sheath proximal and distal ends. The housing and the IC device extension may be initially positioned proximate the sheath distal end. Optionally, the housing and the IC device extension may be moved into the sheath distal end after the sheath distal end has been moved proximate to an implantation site. The IC device extension may be in a collapsed state while in the sheath. The introducer assembly may also include a shape-adjusting member positioned within or over a portion of the sheath. The shape-adjusting member may be configured to be selectively transitioned between a navigation state, in which the sheath is configured to be navigated through vasculature of the patient, and an at-rest state, in which the sheath distal end is configured to be directed toward an implantation site within the heart.

The introducer assembly may also include a guide member operatively connected to the shape-adjusting member. The guide member is configured to selectively transition the shape-adjusting member between the navigation and at-rest states. The guide member may include one or both of a guide wire or guide tube. The guide wire or guide tube may be positioned within a central passage of the shape-adjusting member. The sheath may include flexible bellows proximate the shape-adjusting member.

The introducer assembly may also include a removal wire connected to the shape-adjusting member. The removal wire may be configured to remove the shape-adjusting member from the sheath.

The shape-adjusting member may include at least one hook segment and/or an intermediate curved portion.

The introducer assembly may be configured to implant the IIMD into the heart so that the housing is located in the local chamber, and the IE orientation segment is lodged within the adjacent chamber in order to stabilize the IIMD within heart. The introducer assembly may be configured to implant the IIMD into the heart so the housing is securely anchored within the local chamber, and the IC device extension is securely lodged between wall portions of the adjacent chamber. The introducer assembly may be configured to implant the IIMD into the heart so that an RAA stabilization segment is proximate an RAA of the heart and an IVC stabilization segment is proximate an IVC of the heart.

Certain embodiments of the present disclosure provide an intra-cardiac implantation method configured to implant an intra-cardiac implantable medical device into a heart, wherein the IIMD includes a housing configured to be implanted entirely within a local chamber of the heart, and an intra-cardiac device extension including a proximal end, a distal end, and an extension body extending therebetween, wherein the extension body includes an IE orientation segment connected to a chamber transition segment that is sufficient in length to extend from the local chamber into an adjacent chamber. The method may include positioning the housing and the IC device extension within a sheath distal end of a sheath of an introducer assembly, wherein the positioning operation comprises collapsing the IC device extension within the sheath distal end. The method may also include navigating the introducer assembly through vasculature, adjusting a shape of the introducer assembly with a shape-adjusting member within the adjacent chamber so that the sheath distal end is directed toward an implantation site, holding the shape-adjusting member in position within the sheath, sliding the sheath over the shape-adjusting member, urging the sheath distal end into the implantation site, pushing the housing of the IIMD through the sheath distal end into the implantation site, anchoring the housing into the implantation site, removing the sheath from the IIMD, deploying the extension body within the heart during the removing operation, and stabilizing the IIMD within the heart through the anchoring and deploying operations.

The adjusting operation may include curving the shape-adjusting member so that the sheath distal end is directed toward an implantation site within the local chamber. The adjusting operation may include transitioning the shape-adjusting member from a navigation state to an at-rest state. The adjusting operation may include transitioning the shape-adjusting member from the navigation state to the at-rest state through a guide member.

The method may also include removing the shape-adjusting member from the sheath after the adjusting operation.

The anchoring operation may include anchoring the housing in the local chamber.

The securing operation may include lodging the IE orientation segment within the adjacent chamber in order to stabilize the IIMD within heart. The securing operation may include lodging the IC device between wall portions of the adjacent chamber.

The stabilizing operation may include positioning an RAA stabilization segment of the IE orientation segment proximate a right atrial appendage of the heart and positioning an IVC stabilization segment of the IE orientation segment proximate an inferior vena cava of the heart.

BRIEF DESCRIPTION OF THE DRAWINGS

FIG. 5 illustrates a lateral view of a shape-adjusting member in an at-rest position, according to an embodiment of the present disclosure.

FIG. 6 illustrates a longitudinal view of a shape-adjusting member secured to a guide member, according to an embodiment of the present disclosure.

FIG. 7 illustrates an axial cross-sectional view of a shape-adjusting member and a guide member through line 7-7 of FIG. 6, according to an embodiment of the present disclosure.

FIG. 8 illustrates an axial cross-sectional view of a shape-adjusting member and a guide member, according to an embodiment of the present disclosure.

DETAILED DESCRIPTION

Figure 1:
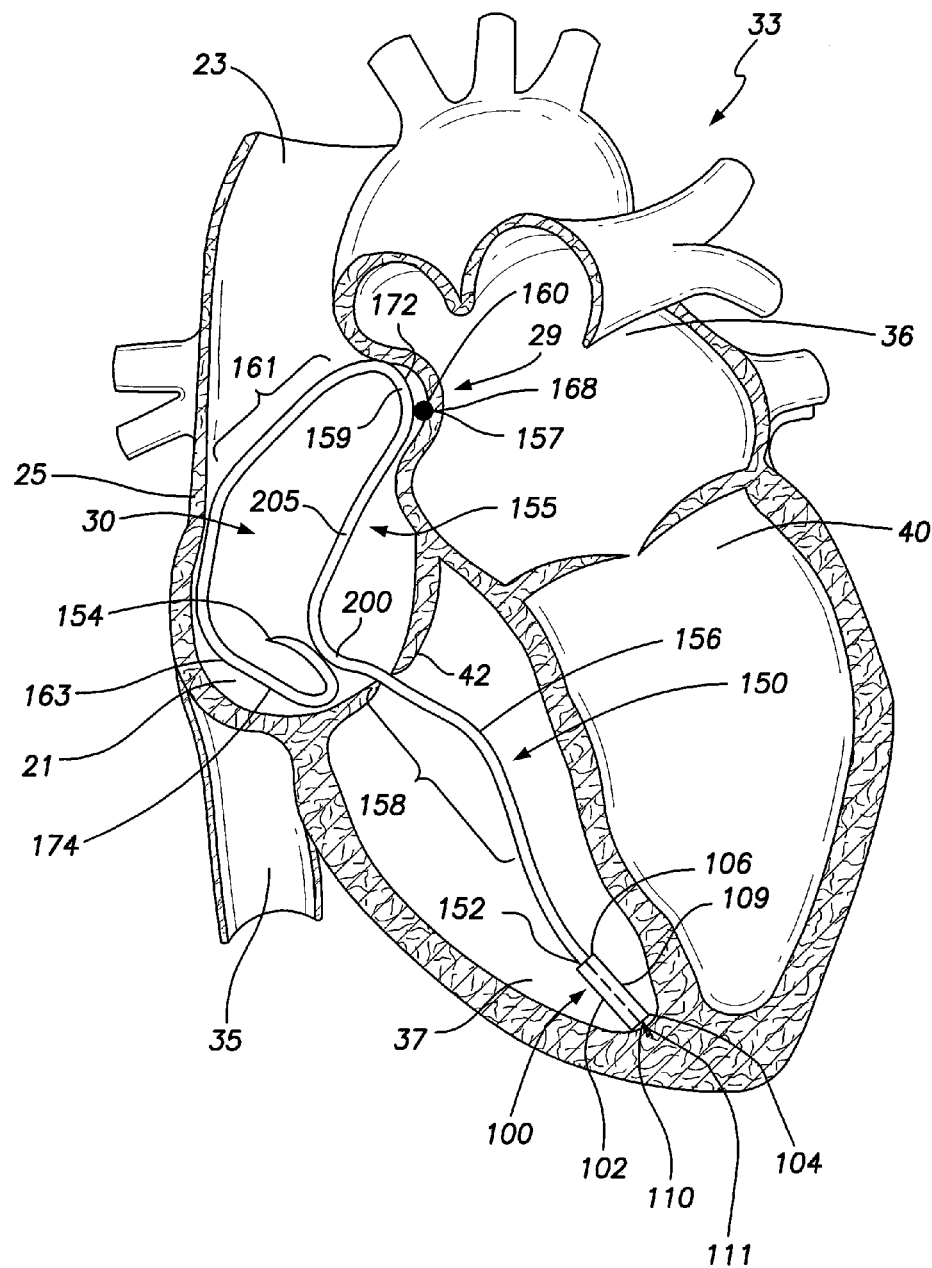
FIG. 1 illustrates a sectional view of a patient's heart having an implantable medical device, according to an embodiment of the present disclosure.

FIG. 1 illustrates a sectional view of a patient's heart 33 having an intra-cardiac implantable medical device (IIMD) 100, according to an embodiment of the present disclosure. The IIMD 100 has been introduced and implanted through the inferior vena cava 35, through the right atrium 30 and into the right ventricle 37 of the heart 33. Alternatively, the IIMD 100 may have been introduced through the superior vena cava 23. As another option, the IIMD 100 may be introduced into the left atrium through a pulmonary vein, into the left ventricle through the intraventricular septum, into the left ventricle through a vein, and the like. The atrial septum divides the two atria 30, 36, while the tricuspid valve 42 is shown between the right atrium 30 and right ventricle 37. FIG. 1 also illustrates the right atrial appendage (RAA) 29. The reader will appreciate that the view of FIG. 1 is simplified and somewhat schematic, but that nevertheless FIG. 1 and the other views included herein suffice to illustrate adequately the placement and operation of certain embodiments. The term "septum" may be used throughout to generally refer to any portion of the heart separating two chambers (for example, right atrium to left atrium, right ventricle to left ventricle, left atrium to left ventricle, right atrium to left ventricle, etc.) The IIMD 100 is formed in accordance with an embodiment and may represent a pacemaker that functions in a DDD-mode, a cardiac resynchronization device, a cardioverter, a defibrillator, or the like. When in DDD-mode, the IIMD 100 may sense in two chambers, pace in two chambers and inhibit pacing in either chamber based on intrinsic events sensed in that chamber or in the other chamber. The IIMD 100 may be configured to be implanted entirely within a single local chamber of the heart. For example, the IIMD 100 may be implanted entirely and solely within the right atrium or entirely and solely within the right ventricle. Optionally, the IIMD 100 may be implanted entirely and solely within the left atrium or left ventricle through more invasive implant methods.

The IIMD 100 may be operated in various modes, such as in select pacemaker modes, select cardiac resynchronization therapy modes, a cardioversion mode, a defibrillation mode, and/or the like. For example, a typical pacing mode may include DDI, DDD, DDO and the like, where the first letter indicates the chamber(s) paced (e.g., A: Atrial pacing; V: Ventricular pacing; and D: Dual-chamber (atrial and ventricular) pacing). The second letter indicates the chamber in which electrical activity is sensed (e.g., A, V, or D). The code O is used when pacemaker discharge is not dependent on sensing electrical activity. The third letter refers to the response to a sensed electric signal (e.g., T: Triggering of pacing function; I: Inhibition of pacing function; D: Dual response (i.e., any spontaneous atrial and ventricular activity will inhibit atrial and ventricular pacing and lone atrial activity will trigger a paced ventricular response) and O: No response to an underlying electric signal (usually related to the absence of associated sensing function).

For convenience, hereafter the chamber in which a housing or can (such as the housing 102) of the IIMD 100 is implanted shall be referred to as the "local" chamber. The local chamber includes a local chamber wall that is physiologically responsive to local activation events originating in the local chamber. The local chamber is at least partially surrounded by local wall tissue that forms or constitutes at least part of a conduction network for the associated chamber. For example, during normal operation, the wall tissue of the right atrium contracts in response to an intrinsic local activation event that originates at the sinoatrial (SA) node and in response to conduction that propagates along the atrial wall tissue. For example, tissue of the right atrium chamber wall in a healthy heart follows a conduction pattern, through depolarization, that originates at the SA node and moves downward about the right atrium until reaching the atria ventricular (AV) node. The conduction pattern moves along the chamber wall as the right atrium wall contracts.

The term "adjacent" chamber shall refer to any chamber separated from the local chamber by tissue (e.g., the right ventricle, left ventricle and left atrium are adjacent chambers to the right atrium; the right atrium and left ventricle are adjacent chambers to the left atrium; the right atrium and right ventricle are adjacent to one another; the right ventricle and left ventricle are adjacent to one another, and the left ventricle and left atrium are adjacent to one another).

The IIMD 100 includes a housing 102 that includes a base 104 and a top end 106. The housing 102 extends along a longitudinal axis 109 between the base 104 and the top end 106. The housing 102 may be elongated and tubular in shape and extends along the longitudinal axis 109. The base 104 is configured to be secured to the local chamber. In the example of FIG. 1, the base 104 may be secured to the right ventricle 37. Optionally, the IIMD 100 may be located in, and the base 104 secured to, the wall of the left ventricle 40, left atrium 36, or right atrium 30.

The base 104 may include an active fixation member 110 provided thereon and extending outward from the base 104 in a direction generally along the longitudinal axis 109. A first electrode 111 (also referred to as an active electrode area) may be provided on the active fixation member 110. The electrode 111 may be provided at a first position such that, when the IIMD 100 is implanted in the local chamber, the first electrode 111 engages the local wall tissue at a local activation site within the conduction network of the local chamber (e.g., within the ventricular wall tissue at the apex of the right ventricle).

The IIMD 100 also includes an intra-cardiac (IC) device extension 150 having a proximal end 152, a distal end 154 and an extension body 156 extending there between. The term "intra-cardiac" is used to indicate that the device extension 150 "generally" remains within the heart 33 and associated vessels, such as the SVC, IVC, CS, pulmonary arteries, and/or the like. The term "device" is used to indicate that the extension 150 is an extension of the IIMD 100. The proximal end 152 may be permanently or removably (through a header style connector) coupled to the housing 102 and located in the local chamber. The extension body 156 may include an IIMD-to-electrode (IE) orientation segment 155 configured to stabilize and secure the IIMD 100 within the heart 33. The IE orientation segment orients an electrode 168 at a desired anatomical location. A right atrial appendage (RAA) fixation mechanism 157 may be provided at an intermediate point along the length of the extension body 156 and aligned with the right atrial appendage 29.

The extension body 156 may include a chamber transition sub-segment 158 integrally connected to the IE orientation segment 155. The transition sub-segment 158 merges into the IE orientation segment 155, which includes a first curved segment 200 that turns at a sharp angle toward the right atrial appendage 29. Optionally, the first curved segment 200 may form an acute angle, right angle, or obtuse angle approximately with respect to a longitudinal axis of the housing 102. The first curved segment 200 merges into and is followed by a first generally linear region 202 that extends toward the right atrial appendage 29 until merging with an RAA stabilizer segment 159 that is lodged or wedged into, or otherwise abuts against the right atrial appendage 29 within the right atrium 30. The RAA stabilizer segment 159 may include an active interim-segment 160 that includes the RAA fixation mechanism 157, such as a helical fixation member, or the like. As shown in FIG. 1, the RAA fixation mechanism 157 extends from the RAA stabilizer segment 159. For example, the RAA fixation mechanism 157 may tangentially extend from a portion of the RAA stabilizer segment 159 and secure directly into tissue of the right atrial appendage 29. Optionally, the RAA fixation mechanism 157 may merely be an electrode that abuts into the right atrial appendage 29.

The RAA stabilizer segment 159 may be an arcuate section that curves and conforms to an interior surface of the right atrium 30 proximate the right atrial appendage 29. The RAA stabilizer segment 159 curves back toward a distal interior wall 25 of the right atrium 30 and integrally connects to a spanning segment 161 that spans from the right atrial appendage 29 to the distal interior wall 25. In turn, the spanning segment 161 integrally connects to an IVC stabilizer segment 163. The IVC stabilizer segment 163 may also be an arcuate section that curves and conforms to the interior surface of the right atrium 30 above and around an opening 21 of the inferior vena cava 35. The IVC stabilizer segment 163 abuts against tissue on opposite sides, for example, of the opening 21 of the inferior vena cava 35. For example, the IVC stabilizer segment 163 may be wedged between the distal interior wall 25 and tissue adjacent the tricuspid valve 42. As shown, the IVC stabilizer segment 163 may not be within the inferior vena cava 35. Alternatively, however, at least a portion of the IVC stabilizer segment 163 may be positioned within the inferior vena cava 35. The distal end 154 of the extension body 156 may curve away from the inferior cava 35 toward a center of the right atrium 30. Accordingly, the extension body 156 is securely wedged, lodged, anchored, or otherwise secured within the right atrium 30 proximate the right atrial appendage 29 and the inferior vena cava 35. As shown in FIG. 1, the IIMD 100 may be secured within the heart 33 at three areas: the housing 102 securely fixed within the right ventricle 37, the RAA stabilizer segment 159 within the right atrium 30 proximate the right atrial appendage 29, and the IVC stabilizer segment 163 proximate the inferior vena cava 35.

The RAA stabilizer segment 159 and the IVC stabilizer segment 163 are exemplary structural implementations of the IE orientation segment 155. The RAA fixation mechanism 157 is one exemplary structural implementation of the active interim-segment 160. The chamber transition segment 158 is sufficient in length to extend from the local chamber (for example, the right ventricle) through the tricuspid valve 42 into an adjacent chamber (for example, the right atrium). The chamber transition segment 158 extends upward out of the right ventricle 37 in a direction that generally follows the longitudinal axis 109 of the housing 102.

The extension body 156 may be formed of a biocompatible insulated material such as EFTE, silicon, OPTIM and the like. In general, the extension body 156 may be formed of materials that are flexible yet exhibit a desired degree of shape memory such that once implanted, the active interim-segment 160, the RAA stabilizer segment 159, and the IVC stabilizer segment 163 are biased to return to a pre-formed shape. One or more insulated conductive wires are held within the extension body 156 and span from the housing 102 to any sensors or electrodes provided on the extension body 156.

The extension body 156 may be pre-formed into a predetermined shape based upon which portion of the chamber is to be engaged. The flexible RAA stabilizer segment 159 may be wrapped into at least one turn 172 having a pre-formed radius. For example, when intended to securely engage the tissue of the right atrial appendage 29, the RAA stabilizer segment 159 may be formed into an arcuate shape with the turn 172 being pre-disposed or biased to radially expand to a diameter sufficient to firmly fit against the right atrial appendage 29. Similarly, the IVC stabilizer segment 163 may be wrapped into at least one turn 174 having a pre-formed radius. When intended to securely engage tissue proximate the opening 21 of the inferior vena cava 35, the IVC stabilizer segment 163 may be formed with one or more turns 174 that radially expand to a different diameter sufficient to firmly fit against the interior walls of the right atrium 30 proximate the inferior vena cava 35.

Optionally, the RAA stabilizer segment 159 and the IVC stabilizer segment 163 may utilize alternative shapes for stabilization, such as an S-shape, a T-shape, a Y-shape, a U-shape and the like. Optionally, the segments 159 and 163 may be split into multiple (for example, 2-4) stabilizer end-segments that project outward in different directions and contact different areas of the wall tissue.

The extension body 156 includes a flexible material having a pre-formed, memorized, permanent implanted state that is shaped to conform to select anatomical contours in the heart and to bias the active interim segment 160 and stabilization arm 155 against the wall tissue at regions of interest. In an embodiment, the curved shape may be configured to follow a contour of an interior of a right atrial appendage. One curved shape may be used for all patients. As another example, prior to implant, the patient's heart may be analyzed to identify the size of one or more chambers of interest and to identify the size and/or shape of the right atrial appendage. In this example, different IC device extensions 150 may be available with different size and/or shape active interim-segments 160. The physician may select the IC device extension 150 that represents the closest match to the size/shape of the patient's chamber in which the IC device extension 150 is to be implanted.

A controller is provided within the housing 102 to cause stimulus pulses to be delivered, in a dual chamber synchronous manner, through the first electrode 111 and a second electrode 168 to the local and distal activation sites, respectively. The stimulus pulses delivered at the distal activation site are timed to cause contraction of the adjacent chamber in a predetermined relation to contraction of the local chamber. For example, the IIMD 100 may be configured to control delivery of the stimulus pulses from the first and second electrodes 111, 168 in accordance with a DDD pacing mode to a right atrium and right ventricle, while the housing 102 is entirely located in one of the right atrium 30 or right ventricle 37. For example, the controller may be configured to control delivery of the stimulus pulses from the first and second electrodes 111, 168 in accordance with a DDD pacing mode to a left atrium and left ventricle, while the housing 102 is entirely located in one of the left atrium and left ventricle.

Optionally, the base 104 may include multiple electrodes 111 securely affixed thereto and projected outward. For example, the electrodes 111 may be formed as large semicircular spikes or large gauge wires. A pair of electrodes 111 may be located on opposite sides of, and wound in a common direction with, an inner electrode (not shown). The electrodes 111 may be provided directly on the housing 102 of the IIMD 100 at a first position, namely at or proximate to a periphery of the base 104 of the housing 102.

The electrodes 111, 168 may be electrically configured to operate as multiple cathode electrodes that are actively fixated or passively held against the wall tissue at a tissue of interest. The electrode 111 may be configured as a screw with a large pitch (e.g. length between adjacent turns), large diameter and may have a length that is relatively short. Optionally, the electrode 111 may be a screw with a small pitch, small diameter and longer length. The screw shape of the electrode 111 is used to firmly adhere to the wall tissue. The electrode 111 may have very little or no insulation material thereon to facilitate a good electrical connection to local wall tissue along the majority or the entire length of the electrode 111 for delivering stimulus pulses and sensing electrical activity in the local chamber where the IIMD 100 is located.

The extension body 156 may be formed as a single elongated body that includes multiple linear regions and curved segments. The elongated body of the extension body 156 may have various cross-sectional shapes, such as disc-shaped, oval, circular, tubular, rectangular, square, polygonal, triangular, and the like. Optionally, the extension body 156 may have a cross-sectional shape that is paddle shaped or flat, semi-circular, donut shaped and the like.

By way of example, the extension body 156 may be formed by curing silicon to a desired crosslink structure to hold a predetermined shape in which the extension body 156 is positioned during curing. Once the extension body 156 is cured to the desired cross link structure, the extension body 156 retains the predetermined "preload" shape. The RAA stabilization segment 159 and the IVC stabilization segment 163, for example, are illustrated in a deployed configuration and may be preloaded against anatomical portions of tissue of interest.

As noted, the extension body 156 may be formed with shape memory characteristics that allow the extension body 156 to transform between a collapsed state, and an expanded state, in which the extension body 156 assumes a multiple curved shape. In one embodiment, the curved configuration of the extension body 156 includes multiple sharply curved segments, obtusely curved segments, generally linear regions and the like. The number, length, and order of the segments and regions, as well as the degree to which individual segments or regions are curved or linear may vary depending upon the anatomical contour to be followed.

Figure 2:
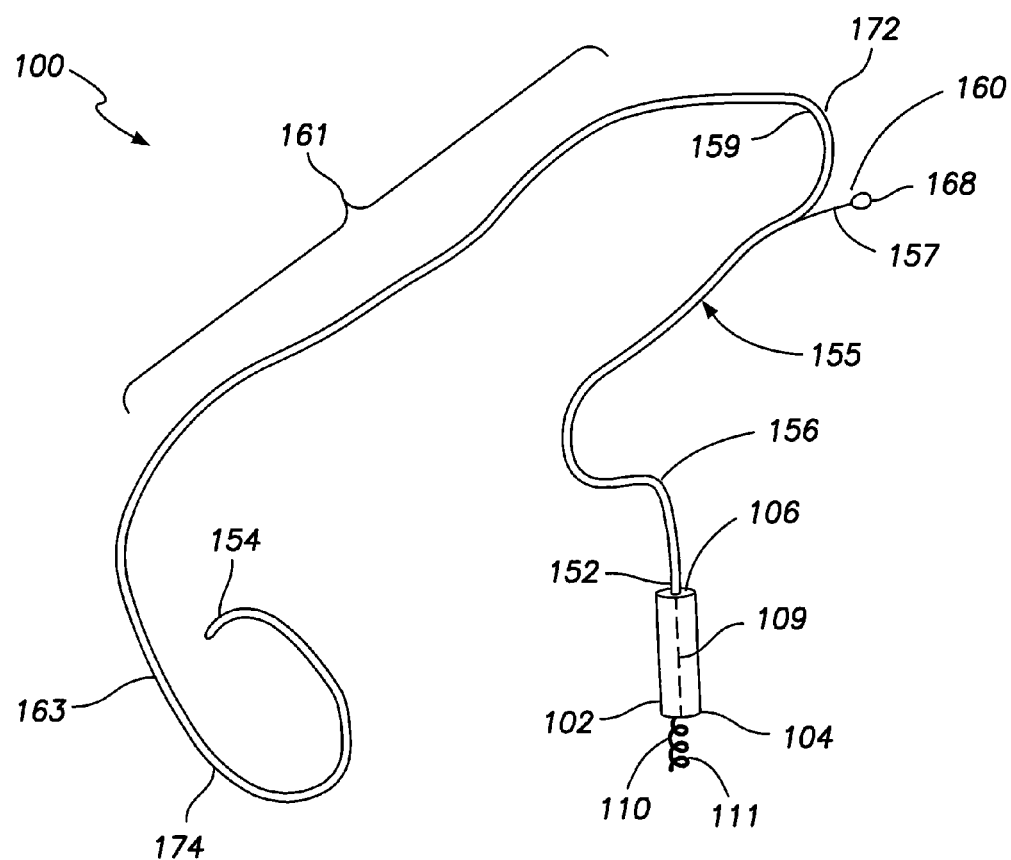
FIG. 2 illustrates a simplified view of an implantable medical device, according to an embodiment of the present disclosure.

FIG. 2 illustrates a simplified view of the IIMD 100, according to an embodiment of the present disclosure. When outside of the heart, the IIMD 100 has an at-rest position, which is shown in FIG. 2. The at-rest position of the IIMD 100 is configured to ensure that the RAA stabilizer segment 159 and the IVC stabilizer segment 163 abut securely into the right atrial appendage 29 (shown in FIG. 1), and areas proximate the opening 21 of the inferior vena cava 35 (shown in FIG. 1). Accordingly, the extension body 156 is formed of a resilient, flexible material that is configured to spring open within the heart 33. As shown in FIG. 2, the at-rest position of the IIMD 100 may be wider, longer, and/or otherwise larger than an interior portion of the heart 33 into which the IIMD 100 is to be implanted. The expanded at-rest position ensures that the IIMD 100 makes adequate contact with the interior portions of the heart 33 described above. For example, the extension body 156 may be a spring member that is biased against walls of the heart 33 by virtue of forces exerted by the extension body 156 that tend to move the extension body toward the at-rest position.

Figure 3:
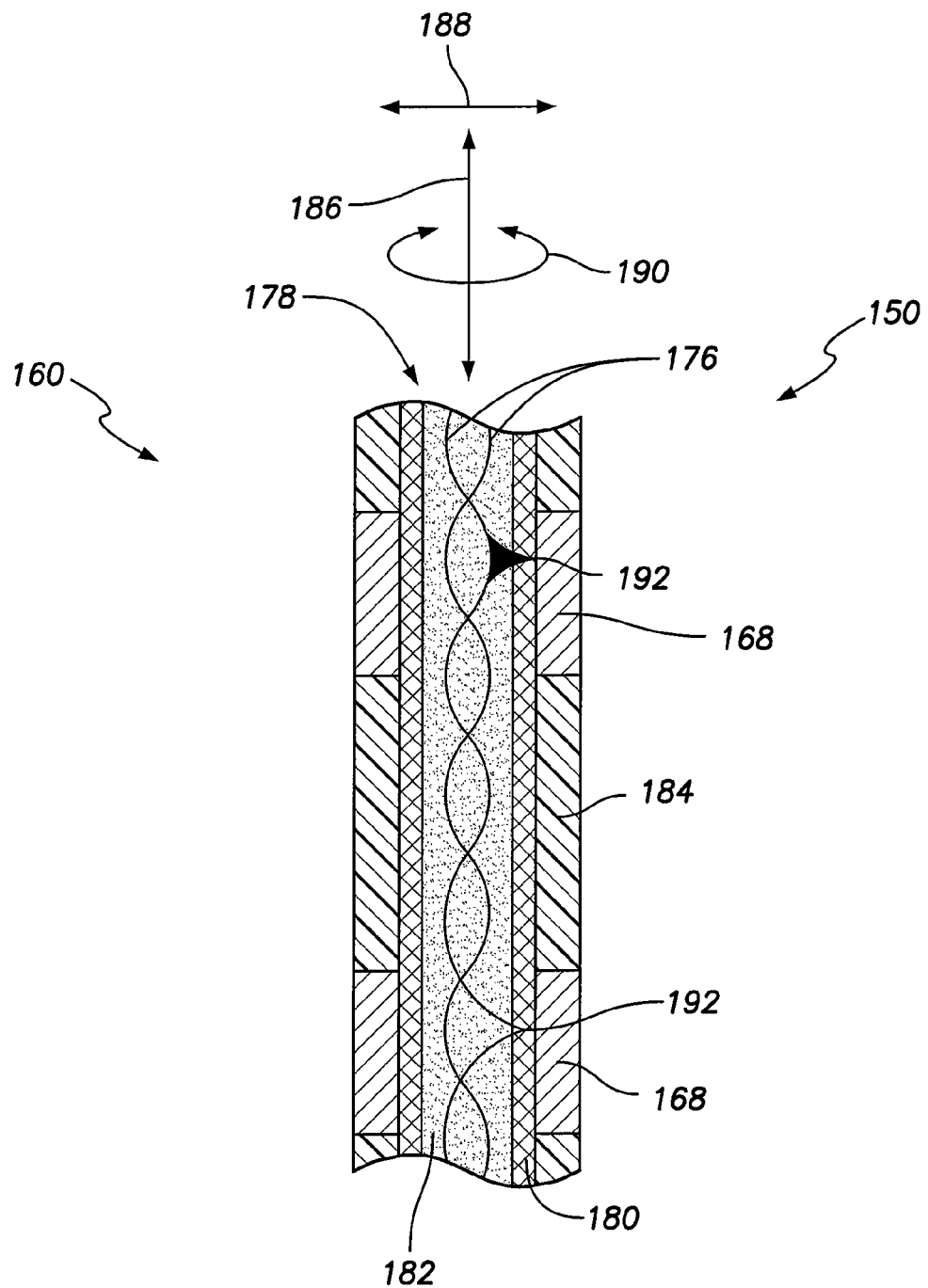
FIG. 3 illustrates a cross section of an active interim-segment of an intra-cardiac device extension, according to an embodiment of the present disclosure.

FIG. 3 illustrates a cross section of the active interim-segment 160 of the IC device extension 150, according to an embodiment of the present disclosure. The active interim-segment 160 may include one or more insulated conductors 176 that are connected to corresponding electrodes 168. The conductors 176 may be connected through a switch to electronics within the IIMD 100 to perform sensing and/or deliver stimulus pulses. The conductors 176 may be wound about one another in a helical manner. The conductors 176 extend along a core 178 and the conductors 176 are radially surrounded by an elongated braid 180. The braid 180 may be made of steel or wire mesh, or have a honeycomb pattern that resists compression or extension along the length of the extension body (as denoted by longitudinal direction 186). The braid 180 is flexible in a lateral direction 188 and may have a spring or force constant that is configured to provide an at-rest shape to the IC device extension 150, such as shown in FIG. 2. The entire length of the IC device extension 150 may be formed of the braid 180. The mesh or honeycomb configuration of the braid 180 may afford strong resistance to torque about the length of the extension body 156 when turned in the rotational direction 190 about the longitudinal direction 186. It is desirable to be resistant to torque in order that, during implant, when a rotational force is applied to one end of the extension body 156, substantially all of such rotational force is conveyed along the length of the extension body 156 to the opposite end. The braid 180 is configured to facilitate delivery of rotational forces and longitudinal pressure to the IIMD 100 during implant.

Optionally, the extension body 156 may further include an insulation material 182 provided around the conductors 176 and around the braid 180. An insulated, flexible, biocompatible shell 184 may be formed over the braid 180. The electrodes 168 are connected to separate corresponding conductors 176 at contacts 192. The electrodes 168 may be formed as ring electrodes, coil electrodes, pin or bump electrodes and the like. While two electrodes 168 are illustrated, it is understood that only one or more than two electrodes 168 may be provided on the extension body 156. The electrodes 168 may be provided at various points about the perimeter of the extension body 156 and at multiple points along the length of the extension body 156.

The electrodes 168 are separated from the braid 180 by insulation (for example, part of the shell 184). The electrodes 168, braid 180 and conductors 176 may be arranged concentrically with one another in a coaxially configuration.

Figure 4:
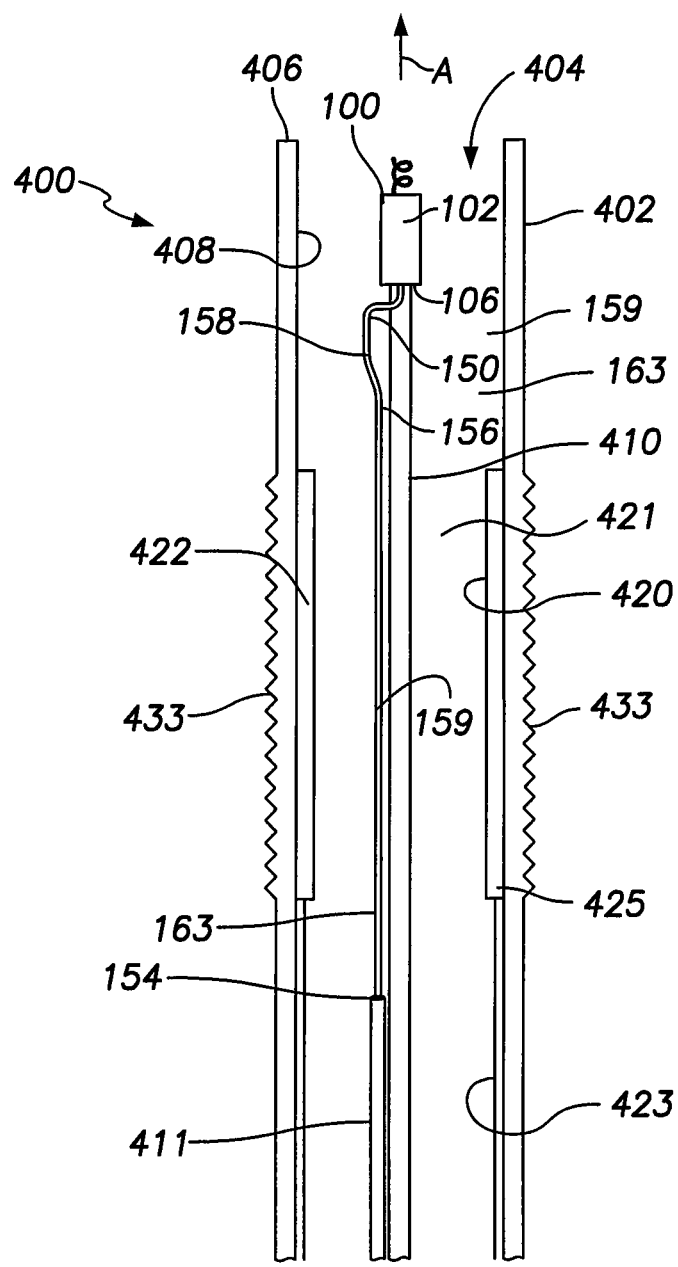
FIG. 4 illustrates a simplified longitudinal axial view of an introducer assembly, according to an embodiment of the present disclosure.

FIG. 4 illustrates a simplified longitudinal axial view of an introducer assembly 400, according to an embodiment of the present disclosure. The introducer assembly 400 includes a flexible, longitudinal, cylindrical open-ended sheath 402 defining a central internal passage 404. The sheath 402 may be a flexible tube formed of rubber, for example, that is configured to be maneuvered through patient vasculature, such as veins and the heart. In this respect, the sheath 402 may be similar to that of a cardiac catheter.

A physician or surgeon operates user controls on the introducer assembly 400 at a proximal end (not shown). The proximal end may include user controls that allow the sheath 402 to be bent, curved, canted, rotated, twisted, or the like, so as to be navigated through a patient's vasculature. For example, a distal end 406 of the sheath 402 may be bent, curved, canted, rotated, twisted, articulated, or the like through operation by the physician or surgeon manipulating the user controls at the proximal end of the introducer assembly 400.

Before and during implantation, the IIMD 100 may be held in the distal end 406 of the sheath 402. For the sake of clarity and simplicity, the size and shape of the IIMD 100 within the introducer assembly 400 is not to scale. The housing 102 of the IIMD 100 may be configured to slide along inner walls 408 of the sheath 402. The IIMD 100 is configured to be pushed out of, or ejected from, the sheath 402 in the direction of arrow A. The top end 106 of the housing 102 of the IIMD 100 connects to the IC device extension 150, which may be compressed and collapsed within the sheath 402. The IC device extension 150 may be disposed along the length of a tool 410. For example, the IC device extension 150 may be linearly stretched over a portion of the length of the tool 410, or may be coiled along a portion of the length of the tool 410. The proximal end 152 is coupled to the housing 102 of the IIMD 100. The extension body 156 extends between the proximal and distal ends 152, 154. The extension body 156 includes the chamber transition sub-segment 158, the RAA stabilizer segment 159, and the IVC stabilizer segment 163, all of which may be stretched, compressed, collapsed, compacted or the like within the internal passage 404 of the sheath 402. Because the extension body 156 may be stretched, compressed, collapsed, compacted, or the like within the internal passage 404, the extension body 156 exerts forces directed toward the inner walls 408 of the sheath 402, but is stretched by a tool 411. When released from the sheath 402, the spring or force constants of the extension body 156 causes it to expand toward its at-rest state, as shown in FIG. 2. As noted above, the extension body 156 may be formed of materials that are flexible, yet offer good shape memory such that the extension body 156 may be compressed while within the sheath 182 and, when removed from the sheath 182, expands or otherwise returns to its original (normal, resting) shape as shown in FIG. 2.

The top end 106 or any other portion of the housing 102 may be connected to the tool 410, such as a pusher, rotator, articulator and/or other such tool configured to selectively attach and detach from the housing 102 in order to implant the housing 102 within the heart 33 (shown in FIG. 1). Additionally, the distal end 154 of the IC device extension 150 may be connected to the tool 411, such as a pusher, rotator, articular, and/or other such tool configured to selectively attach and detach from the distal end 154 in order to properly place and orient the IC device extension within the heart 33 (shown in FIG. 1). For example, the tools 410 and 411 may be or include any of the connection and implantation systems, devices, assemblies or the like, as described in any of U.S. patent application Ser. No. 13/352,048, filed Jan. 17, 2012, entitled "Single-Chamber Leadless Intra-Cardiac Medical Device With Dual-Chamber Functionality"; U.S. patent application Ser. No. 13/669,168, filed Nov. 5, 2012, entitled "Leadless Implantable Medical Device with Dual Chamber Sensing Functionality"; U.S. patent application Ser. No. 13/352,147, filed Jan. 17, 2012, entitled "Leadless Intra-Cardiac Medical Device with Built-In Telemetry System"; U.S. patent application Ser. No. 13/352,136, filed Jan. 17, 2012, entitled "Dual-Chamber Leadless Intra-Cardiac Medical Device with Intra-Cardiac Extension"; U.S. patent application Ser. No. 13/352,005, filed Jan. 17, 2012, entitled "Multi-Piece Dual-Chamber Leadless Intra-Cardiac Medical Device and Method of Implanting Same"; U.S. patent application Ser. No. 13/352,167, filed Jan. 17, 2012, entitled "Unitary Dual-Chamber Leadless Intra-Cardiac Medical Device and Method of Implanting Same"; U.S. patent application Ser. No. 13/352,101, filed Jan. 17, 2012, entitled "Single-Chamber Leadless Intra-Cardiac Medical Device with Dual Chamber Functionality and Shaped Stabilization Intra-Cardiac Extension"; and/or U.S. application Ser. No. 13/547,791, filed Jul. 12, 2012, entitled, entitled "System and Method of Implanting a Medical Device", all of which are hereby incorporated by reference in their entireties.

A shape-adjusting member 420, such as an obturator, flexible hook, stiffening sleeve or insert, or the like, may also be within the internal passage 404 of the sheath 402. The shape-adjusting member 420 may be a tube-like member having an internal passage 421 that is coaxial with the central internal passage 404 of the sheath 402. The tools 410, 411 and the IIMD 100 are able to be positioned within and pass through the central internal passage 421. Optionally, the shape-adjusting member 420 may be on the outside of the sheath 402. Also, alternatively, the shape-adjusting member 420 may be planar or linear strips within or on the sheath 402.

The shape-adjusting member 420 may be formed of a flexible material that may be more rigid than that of the sheath 402. The shape-adjusting member 420 defines the shape of the sheath 402 proximate areas in or on the sheath 402 which the shape-adjusting member 420 is positioned. As shown in FIG. 4, the shape-adjusting member 420 is linear. The linear shape of the shape-adjusting member 420 may be dictated by a guide member 422 that may be removably secured to the shape-adjusting member 420. The guide member 422 may be a guide wire, tube, or the like formed of a stiff material, such as metal, stiff plastic, or the like. As such, when secured to the shape-adjusting member 420, the guide member 422 controls the shape of the shape-adjusting member 420. The guide member 422 may be removably secured to the shape-adjusting member through a threadable connection, tabs and slots, latches, or various other connections.

Alternatively, instead of being removably secured to the shape-adjusting member 420, the guide member 422 may be permanently secured thereto. The guide member 422 may be controlled by the user controls of the introducer assembly 400 in order to move the shape-adjusting member 420 between the at-rest state and other positions. For example, as the guide member 422 is tightened with respect to an attachment point near its proximal end (not shown), the shape-adjusting member 420 may be straightened. As tension in the guide member 422 is decreased, the shape-adjusting member 420 may move toward its at-rest position.

The portion of the sheath 402 surrounding the shape-adjusting member 420 may include flexible bellows 433, similar to that of an accordion, or portion of a drinking straw that allows for articulation. Thus, as the shape adjusting member 420 moves, the bellows 433 may provide a more flexible area of the sheath 402 that is configured to move easily with the underlying shape-adjusting member 420.

A removal wire 423 may be securely attached to a proximal end 425 of the shape-adjusting member 420. A distal end (not shown) of the removal wire 423 may be operatively connected to user controls of the introducer assembly 400. The user controls may be operated to secure the shape adjusting member 420 within the sheath through the removal wire 423, and later remove the shape-adjusting member 420 out of the sheath 402 through the removal wire 423. Alternatively, the shape-adjusting member 420 may not be connected to a removal wire.

As shown in FIG. 5, the shape-adjusting member 420 is in a navigation state. In the navigation state, the shape-adjusting member 420 and the distal end 406 of the sheath 402 may be relatively straight, so that sheath 402 may be safely and easily navigated through vasculature of the patient.

FIG. 5 illustrates a lateral view of the shape-adjusting member 420 in an at-rest position, according to an embodiment of the present disclosure. As shown in FIG. 5, the guide member 422 is removed from the shape-adjusting member 420. As the guide member 422 is removed from the shape-adjusting member 420, the shape-adjusting member 420 moves into the at-rest state or position, as shown.

In the at-rest position, the shape-adjusting member 420 includes a proximal end 424 connected to a distal end 426 through an intermediate hook segment 428. The proximal end 424 includes a straight segment 427 that integrally connects to the intermediate hook segment 428. The intermediate hook segment 428 curves away from a longitudinal axis 430 of the straight segment at an angle θ. The distal end 426 tends to curve inwardly back toward the longitudinal axis longitudinal axis 430 due to the curvature of the hook segment 428. The hook segment 428 curves through an arc β, which may be between 90°-180°, for example. However, the arc β may be greater or less than 90° or 180°. As shown in FIG. 5, in the at-rest position, the shape-adjusting member 420 may be shaped akin to a shepherd's staff. The at-rest position of the shape adjusting member 420 is configured to allow the introducer assembly 400 to deliver the IIMD 100 to a target implantation site. For example, in the at-rest state, the shape-adjusting member 420 is configured to direct the distal end 406 of the sheath 406 toward an implantation site within the heart.

FIG. 6 illustrates a longitudinal axial view of the shape-adjusting member 420 secured to the guide member 422, according to an embodiment of the present disclosure. The guide member 422 stiffens the shape-adjusting member 420 and forces the shape-adjusting member 420 into a relatively linear shape.

FIG. 7 illustrates a cross-sectional view of the shape-adjusting member 420 and the guide member 422 through line 7-7 of FIG. 6, according to an embodiment of the present disclosure. The guide member 422 may be a metal wire removably secured within a reciprocal channel 440 formed through an outer surface 442 of the shape-adjusting member 420. The guide member 422 includes a proximal end (not shown) operatively connected to user controls (not shown) of the introducer assembly 400 (shown in FIG. 4). The user controls may be operated to remove the guide member 422 from the shape-adjusting member 420. For example, the user controls may be operated to threadably disengage the guide member 422 from the shape-adjusting member 420.

FIG. 8 illustrates a cross-sectional view of a shape-adjusting member 420a and a guide member 422a, according to an embodiment of the present disclosure. In this embodiment, the guide member 422a may be within the shape-adjusting member 420a. The guide member 422a may simply be a metal wire within the internal passage 421a that prevents the shape-adjusting member 420a from moving into an at-rest position. The user controls of the introducer assembly 400 may be operated to remove the guide wire 422a from the internal passage 421a, at which point the shape-adjusting member 420a would move into its at-rest position, such as shown in FIG. 5.

Figure 9:
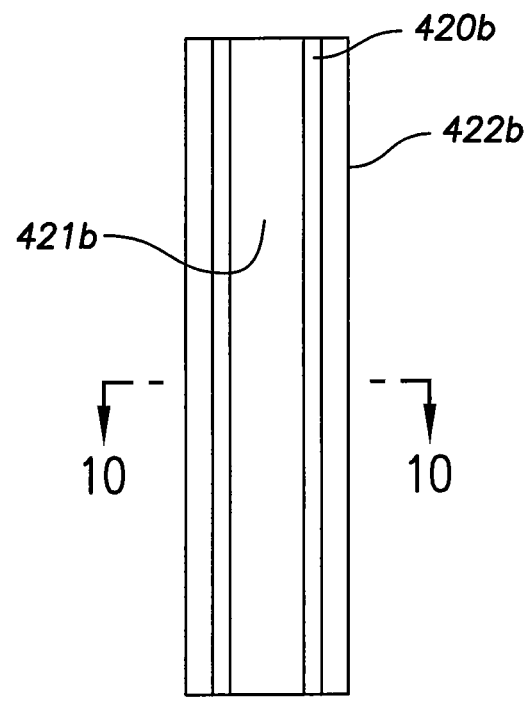
FIG. 9 illustrates a longitudinal cross-sectional view of a shape-adjusting member and a guide member, according to an embodiment of the present disclosure.
Figure 10:
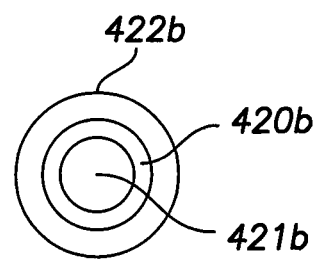
FIG. 10 illustrates an axial cross-sectional view of a shape-adjusting member and a guide member, according to an embodiment of the present disclosure.

FIG. 9 illustrates a longitudinal cross-sectional view of a shape-adjusting member 420b and a guide member 422b, according to an embodiment of the present disclosure. FIG. 10 illustrates an axial cross-sectional view of the shape-adjusting member 420b and the guide member 422b. As shown in FIGS. 9 and 10, the guide member 422b may be a tube or sheath that covers the shape-adjusting member 420b. The guide member 422b may be formed of metal, plastic, an elastomeric material, or the like, that is stiffer than the shape-adjusting member 420b. Alternatively, the guide member 422b may be a stiffening core within the internal passage 421b of the shape-adjusting member 420b. A proximal end of the guide member 422b may be connected to the user controls of the introducer assembly 400, so that the guide member 422b may be removed from the shape-adjusting member 420b.

Referring to FIGS. 5-10, the guide member may be positioned at various portions within or on the shape-adjusting member. For example, the guide member may be a wire within the shape adjusting member. The wire may be coaxial with the shape-adjusting member. Alternatively, the guide member may be a tubular member positioned over or within the shape-adjusting member. The guide member may be detached from the shape adjusting member through the user controls of the introducer assembly 400.

Referring again to FIG. 4, in operation, the distal end 406 of the introducer assembly 400 is inserted into vasculature of a patient, such as a femoral artery, and navigated toward and into the heart 33 (shown in FIG. 1). For example, the introducer assembly 400 is navigated into the inferior vena cava 35 of the heart through the femoral vein.

Figure 11:
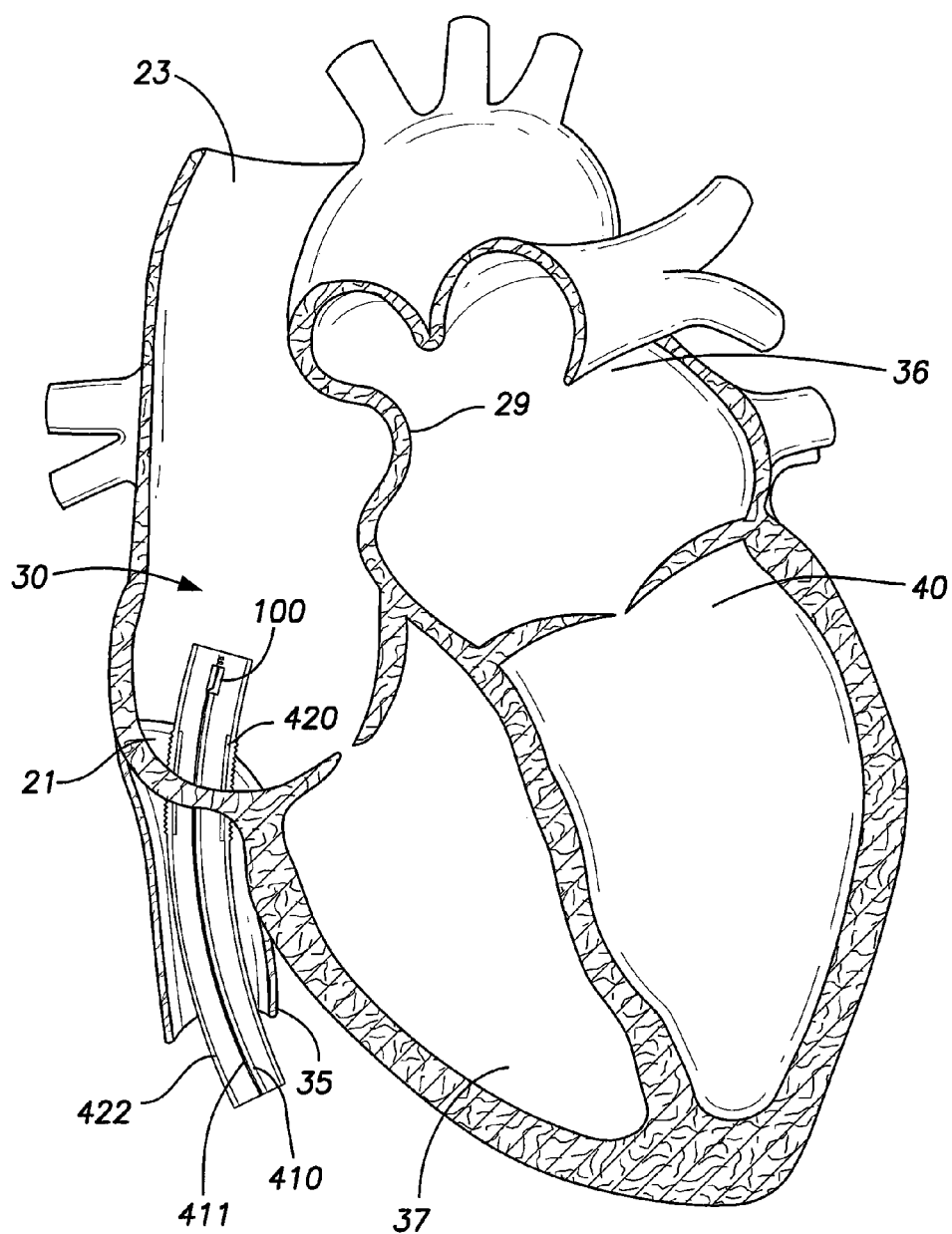
FIG. 11 illustrates a sectional view of a patient's heart with an introducer assembly positioned within an inferior vena cava, according to an embodiment of the present disclosure.

FIG. 11 illustrates a sectional view of the patient's heart 33 with the introducer assembly 400 positioned within the inferior vena cava 35, according to an embodiment of the present disclosure. For the sake or clarity, the introducer assembly 400 is not drawn to scale, and certain internal components, such as the shape-adjusting member 420, are shown, although not to scale. Referring to FIGS. 4 and 11, the guide wire 422 is positioned within the shape-adjusting member 420 to hold the shape-adjusting member 420 straight or relatively linear, so that the introducer assembly 400 may be easily moved and navigated through the vasculature of the patient.

Figure 12A:
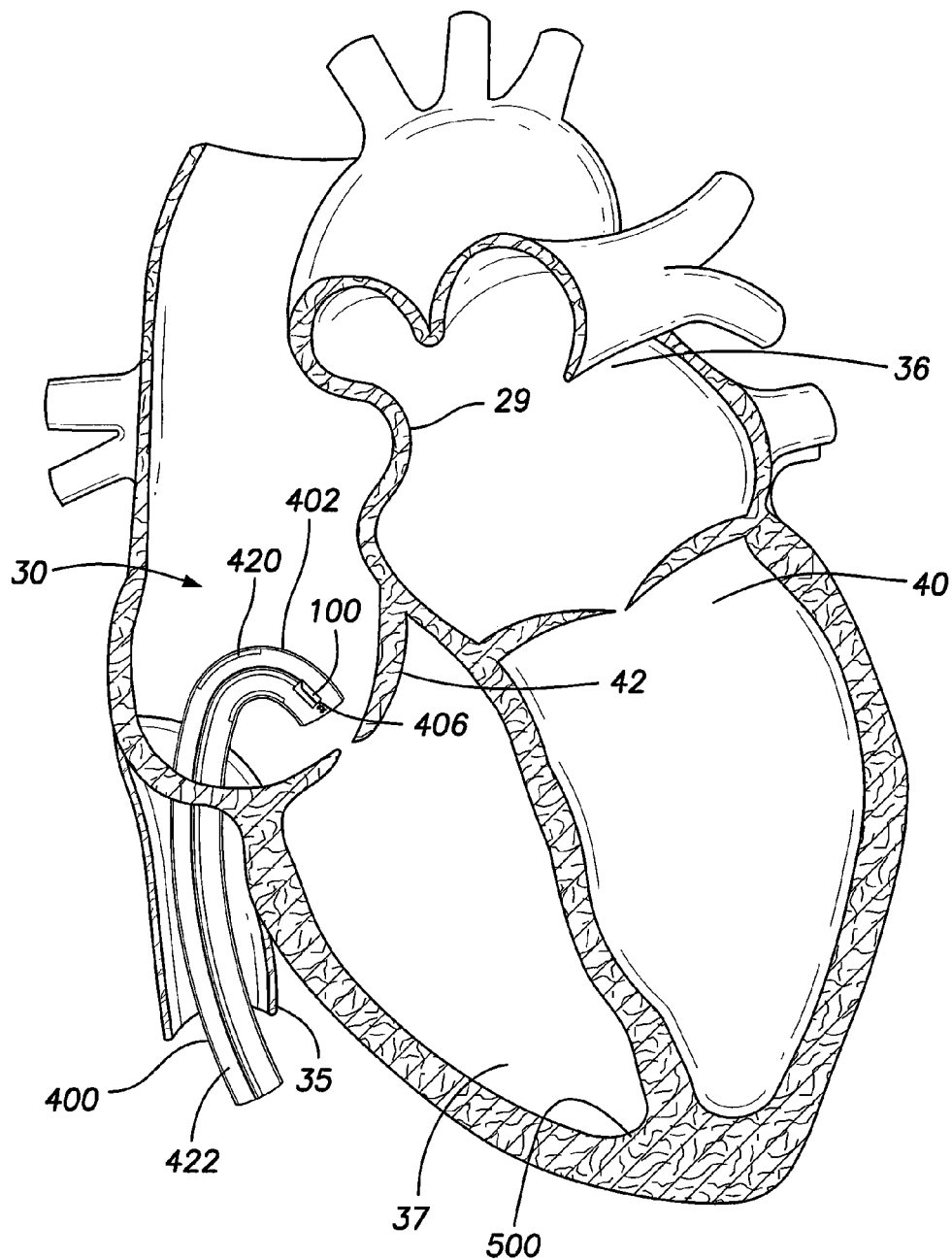
FIG. 12a illustrates a sectional view of a patient's heart with an introducer assembly moved into a right atrium, according to an embodiment of the present disclosure.

FIG. 12a illustrates a sectional view of the patient's heart 33 with the introducer assembly 400 moved into the right atrium 30, according to an embodiment of the present disclosure. As shown, the distal end 406 of the introducer assembly 400 has been bent downward toward the right ventricle by way of the shape-adjusting member 420 being actuated by the guide wire 422 into a bent shape as shown in FIG. 5. After the shape-adjusting member 420 has been actuated as shown in FIG. 12a, the shape-adjusting member 420 may be held in position by the guide wire 422, while the sheath 402 is pushed over the bent shape-adjusting member 420. The user controls of the introducer assembly 400 may be operated to retract the guide wire 422 with respect to the shape-adjusting member 420. As the guide wire 422 retracts, the shape-adjusting member 420 moves into its at-rest position, as shown in FIG. 5, which causes the distal end 406 of the introducer assembly 400 to curve down until pointed toward the tricuspid valve 42, and aligned generally with a desired implantation site 500 within the right ventricle 37. For example, the desired implantation site 500 may be proximate an apex of the right ventricle 37.

Figure 12B:
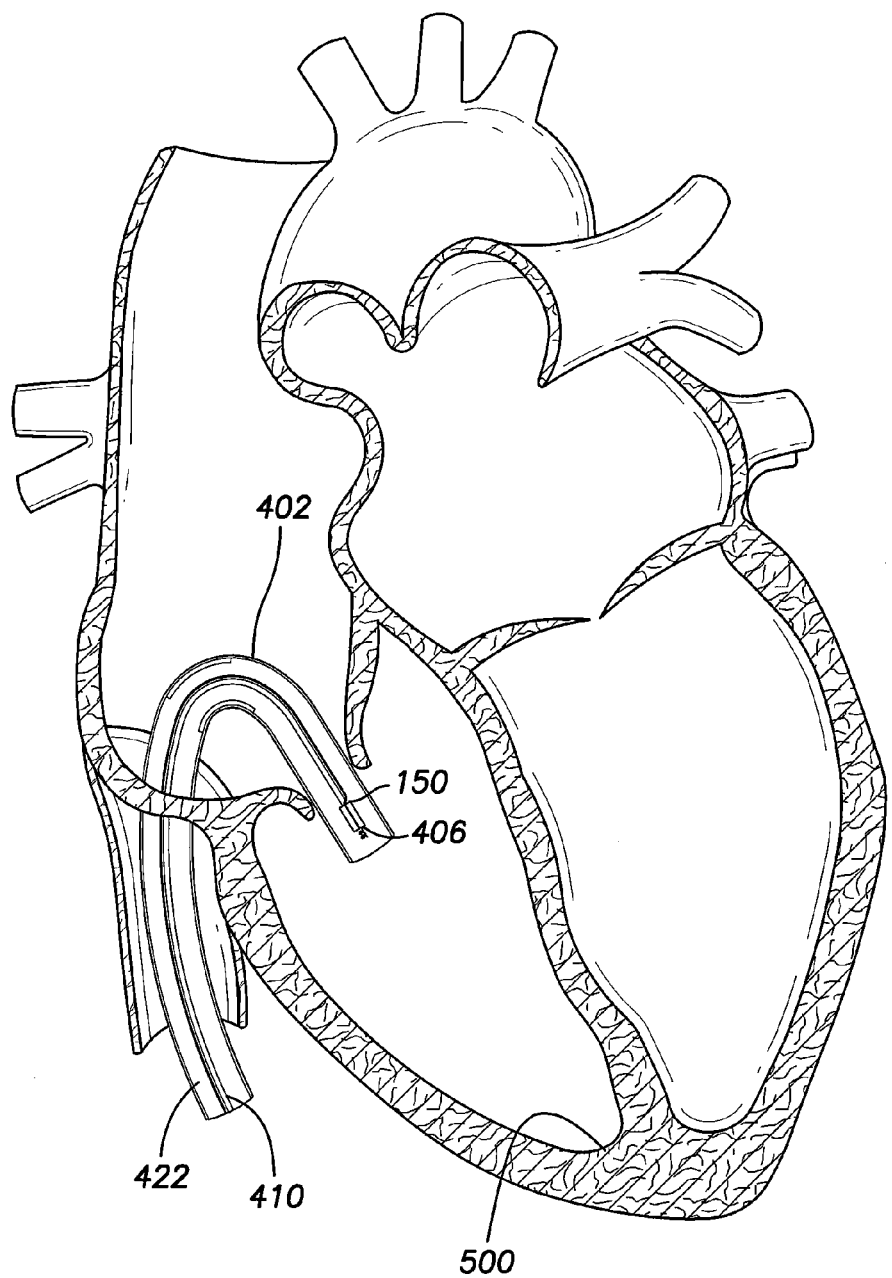
FIG. 12b illustrates a section view of a patient's heat with a sheath of an introducer assembly moved over a shape-adjusting member, according to an embodiment of the present disclosure.

FIG. 12b illustrates a section view of the patient's heat 33 with the sheath 402 of the introducer assembly 400 moved over the shape-adjusting member 420, according to an embodiment of the present disclosure. After the shape-adjusting member 420 has been bent, the sheath 402 is pushed over the shape adjusting member 420 so that the distal end 406 is urged toward an implantation site 500. As the moving sheath 402 slides over the shape-adjusting member 420, the portion of the sheath 402 over the shape-adjusting member 420 follows the curve dictated by the shape-adjusting member 420. The removal wire 422 may hold the shape-adjusting member 420 in place, and prevent the shape-adjusting member 420 from moving while the sheath 402 slides over the shape-adjusting member 420. As the sheath 402 slides over the shape-adjusting member 420, the tools 410 and 411 may move the IIMD 100 and the IC device extension 150 along with the distal end 406 of the sheath 402. Alternatively, the IIMD 100 and the IC device extension 150 may remain proximate to the shape-adjusting member 420, while the distal end 406 is moved into the implantation site 500, at which point the tools 410 and 411 may move the IIMD 100 and IC device extension 150 toward the implantation site 500.

Figure 13A:
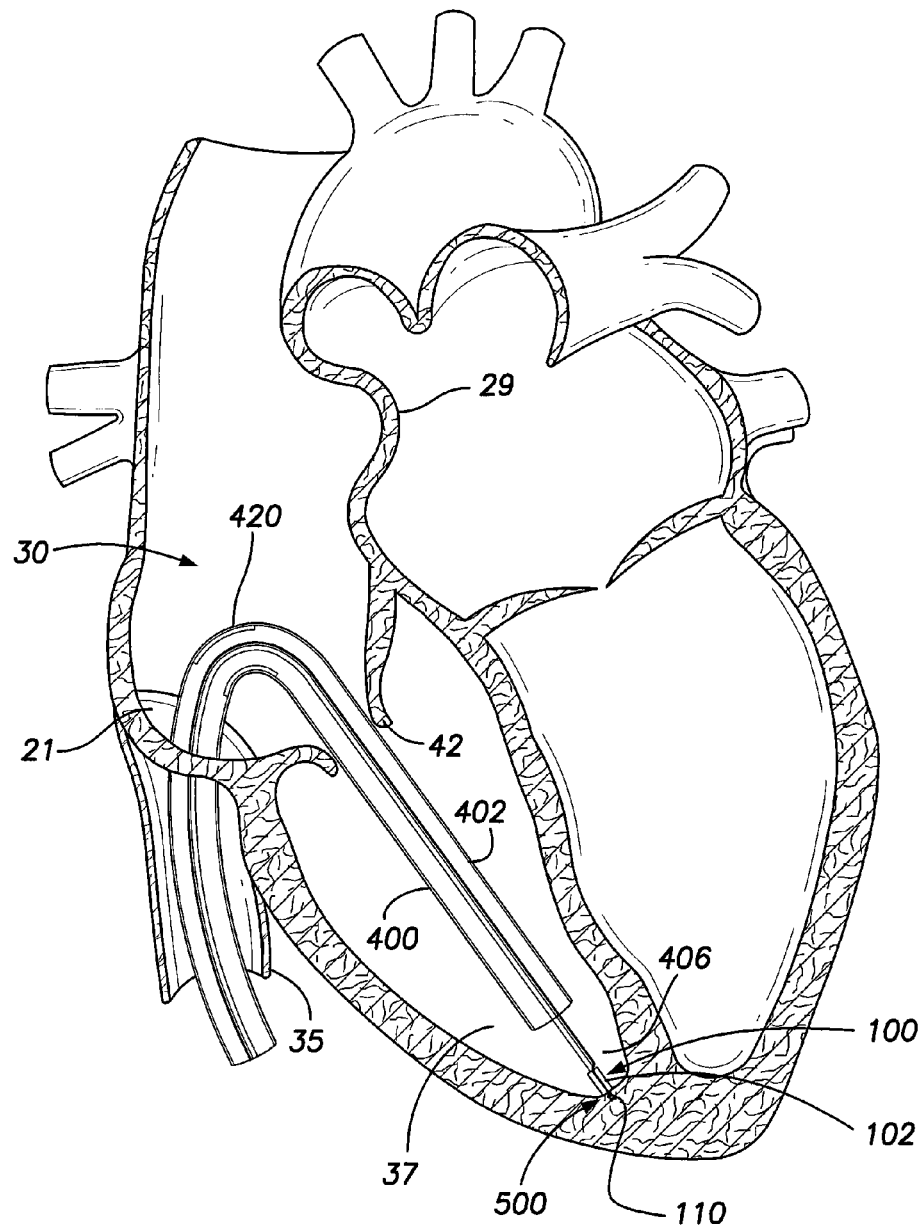
FIG. 13a illustrates a sectional view of a patient's heart with an introducer assembly proximate an implantation site within a right ventricle, according to an embodiment of the present disclosure.

FIG. 13a illustrates a sectional view of the patient's heart 33 with the introducer assembly 400 proximate the implantation site 500 within the right ventricle 37, according to an embodiment of the present disclosure. Referring to FIGS. 4 and 13a, the introducer assembly 400 was previously bent by the shape-adjusting member 420 so that the distal end 406 is oriented toward the implantation site 500 within the right ventricle 37. The introducer assembly 400 is then moved into an abutting relationship with the implantation site 500, at which point, the user controls of the introducer assembly 400 are operated to push the active fixation member 110 of the housing 102 into the implantation site 500. The user controls are further operated to anchor the housing 102 into the implantation site 500 by way of the active fixation member 110. Once the housing 102 is anchored in place, the user controls are operated to pull the sheath 402 and the introducer assembly 400 off of the IIMD 100 (as the housing 102 is anchored in place at the implantation site 500). As the introducer assembly 400 is pulled off of the IIMD 100, the extension body 156 is exposed and begins to expand to its at-rest position.

Figure 13B:
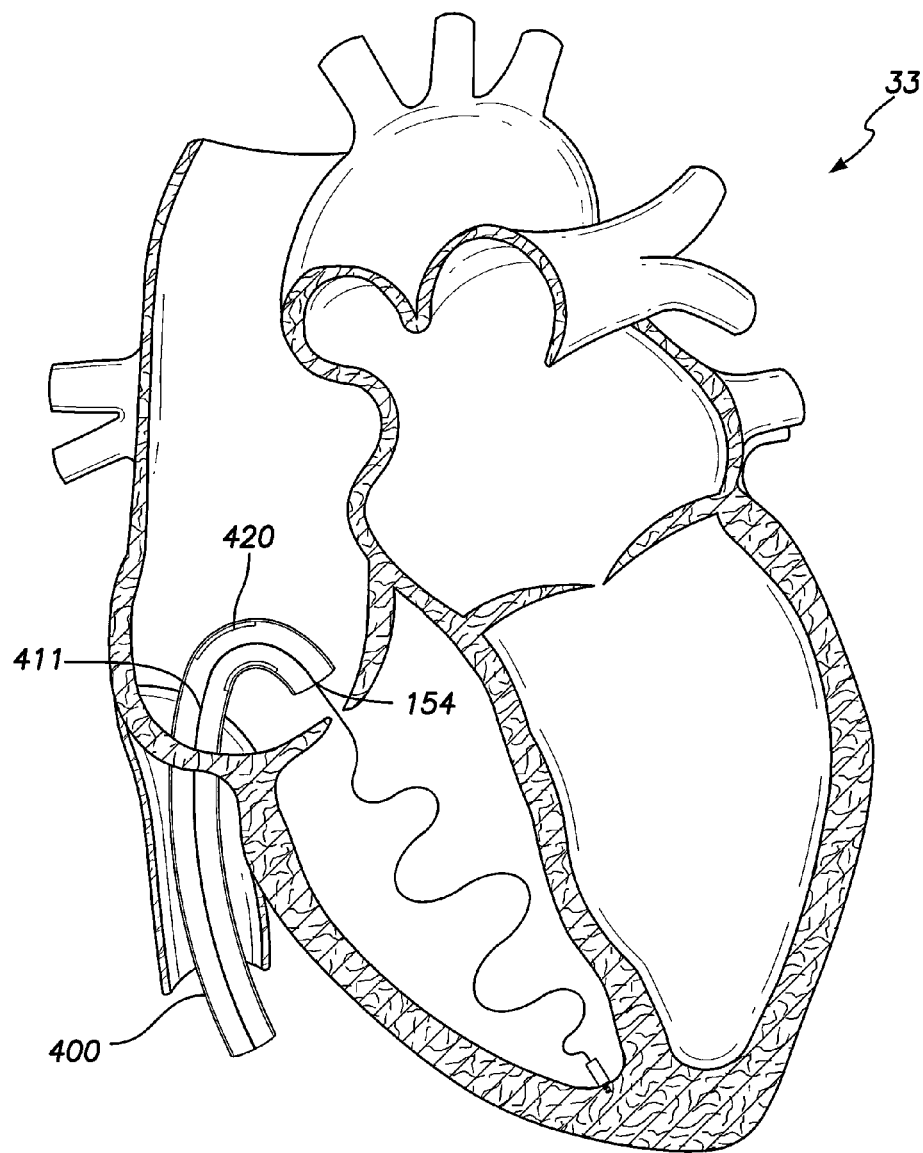
FIG. 13b illustrates a sectional view of a patient's heart with an introducer assembly pulling away from an IIMD, according to an embodiment of the present disclosure.

FIG. 13b illustrates a sectional view of the patient's heart 33 with the introducer assembly 400 pulling away from the IIMD 100, according to an embodiment of the present disclosure. As the introducer assembly 400 is pulled off the IIMD 100 through the tricuspid valve 42, the extension body 156 begins to spring out of the distal end 406, or otherwise deploy. The distal end 154 of the IC device 150 remains secured to the tool 411.

Figure 13C:
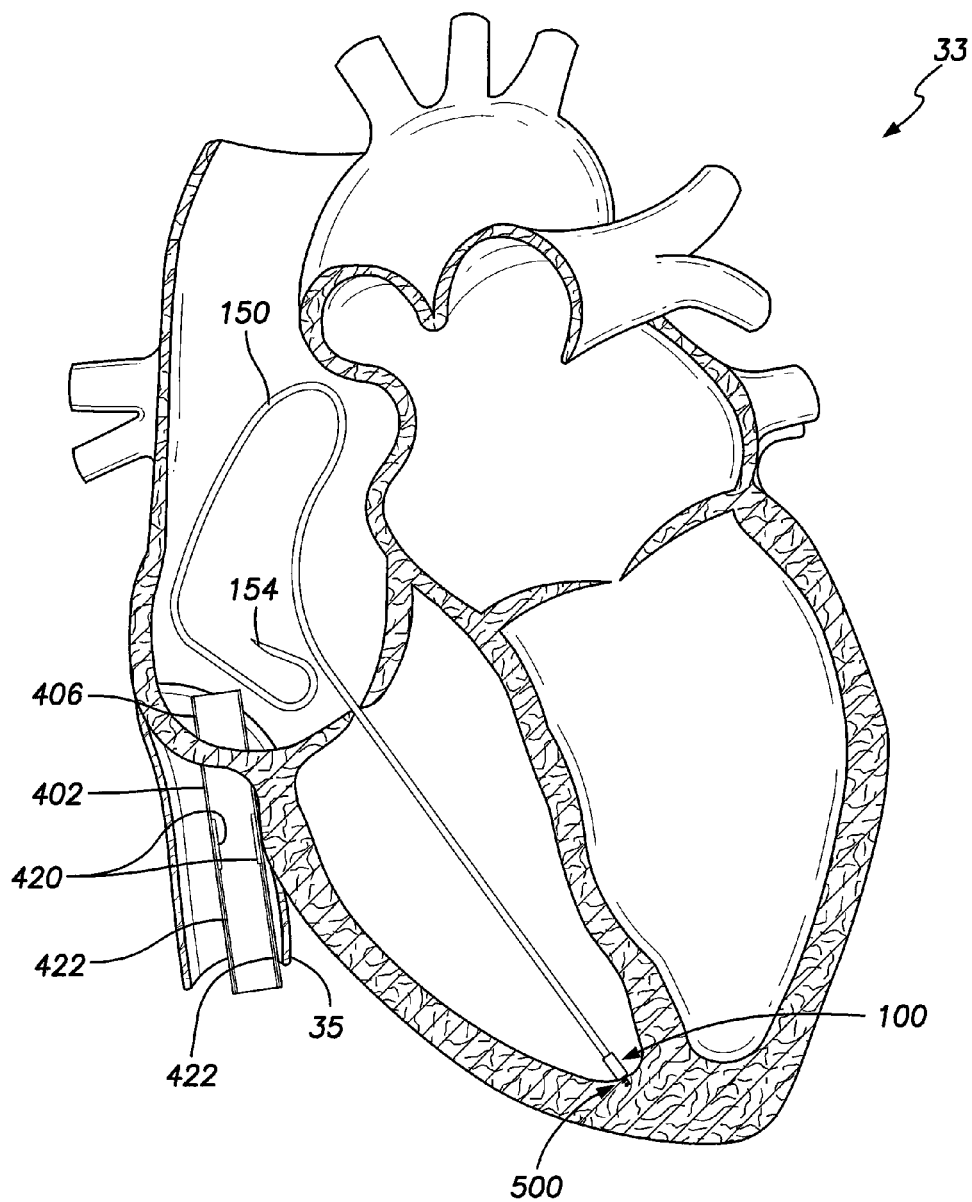
FIG. 13c illustrates a sectional view of a patient's heart with an IC device extension fully out of an introducer assembly, according to an embodiment of the present disclosure.

FIG. 13c illustrates a sectional view of the patient's heart 33 with the IC device extension 150 fully out of the introducer assembly 400, according to an embodiment of the present disclosure. As shown, the shape-adjusting member 400 has been straightened. For example, the guide member 422 may re-engage and straighten the shape-adjusting member 420. Further, the distal end 406 of the sheath 402 may have been pulled back over the shape-adjusting member 420 so that the shape-adjusting member 420 is proximate the distal end 406. Optionally, the shape-adjusting member 420 may have been removed from the sheath 402, such as with the removal wire 423, after the IIMD 100 is anchored to the implantation site 500. In either case, the sheath 402 is then pulled out of the inferior vena cava 35. However, the IIMD 100 is anchored to the implantation site 500, thereby pulling the IC device extension 150 out of the distal end 406 of the sheath 406. The tool 411 remains secured to the distal end 154 of the IC device extension 150. The tool 411 is then used to properly place and orient the IC device extension 150 within the heart 33, as shown in FIG. 1. Once the IC device extension device 150 is properly positioned and oriented, the user controls of the introducer assembly 400 are used to disconnect the tool 411 from the distal end of the IC device extension 150.

Referring again to FIG. 1, the tool 411 positions and orients the IC device extension 150 so that the RAA stabilizing segment 159 lodges into the right atrial appendage 29, and the IVC stabilizing segment 163 lodges into the tissue around the opening 21 of the inferior vena cava 35. As the introducer assembly 400 is further moved out of the heart 33 through the inferior vena cava 35, the IIMD 100 is secured in position by the active fixation member 110 at the implantation site, the RAA stabilizing segment 159 at the right atrial appendage 29, and the IVC stabilizing segment 163 proximate the inferior vena cava 35, as shown in FIG. 1.

Alternatively, the IIMD 100 may not be initially loaded into the sheath 402. Instead, the sheath 402 may be guided into the patient's heart 33 without the IIMD 100. The distal end 406 of the sheath 402 is guided into position as described above. Once the distal end 406 is proximate to, such as abutting into, the implantation site 500, the shape-adjusting member 420 may be removed, such as described above. The flexible bellows 433 (as shown in FIG. 4) may maintain the sheath 402 in the bent position, such as shown in FIG. 13a. For example, the flexible bellows 433 may be configured to provide a bent position after the shape-adjusting member 420 is removed. After the distal end 406 of the sheath 402 is positioned with respect to the implantation site 500, and the shape-adjusting member 420 has been removed, the IIMD 100 may be loaded into the sheath 402 and urged therethrough until it engages the implantation site 500, as described above. Thus, in this embodiment, the introducer assembly 400 is moved into the heart 33 and positioned with respect to the implantation site 500. Then, the shape-adjusting member 500 is removed, and the IIMD 100 is then moved through the introducer assembly 400, through the sheath 402, and into the implantation site 110. The sheath 402 is then removed from the IIMD 100 as described above.

Figure 14:
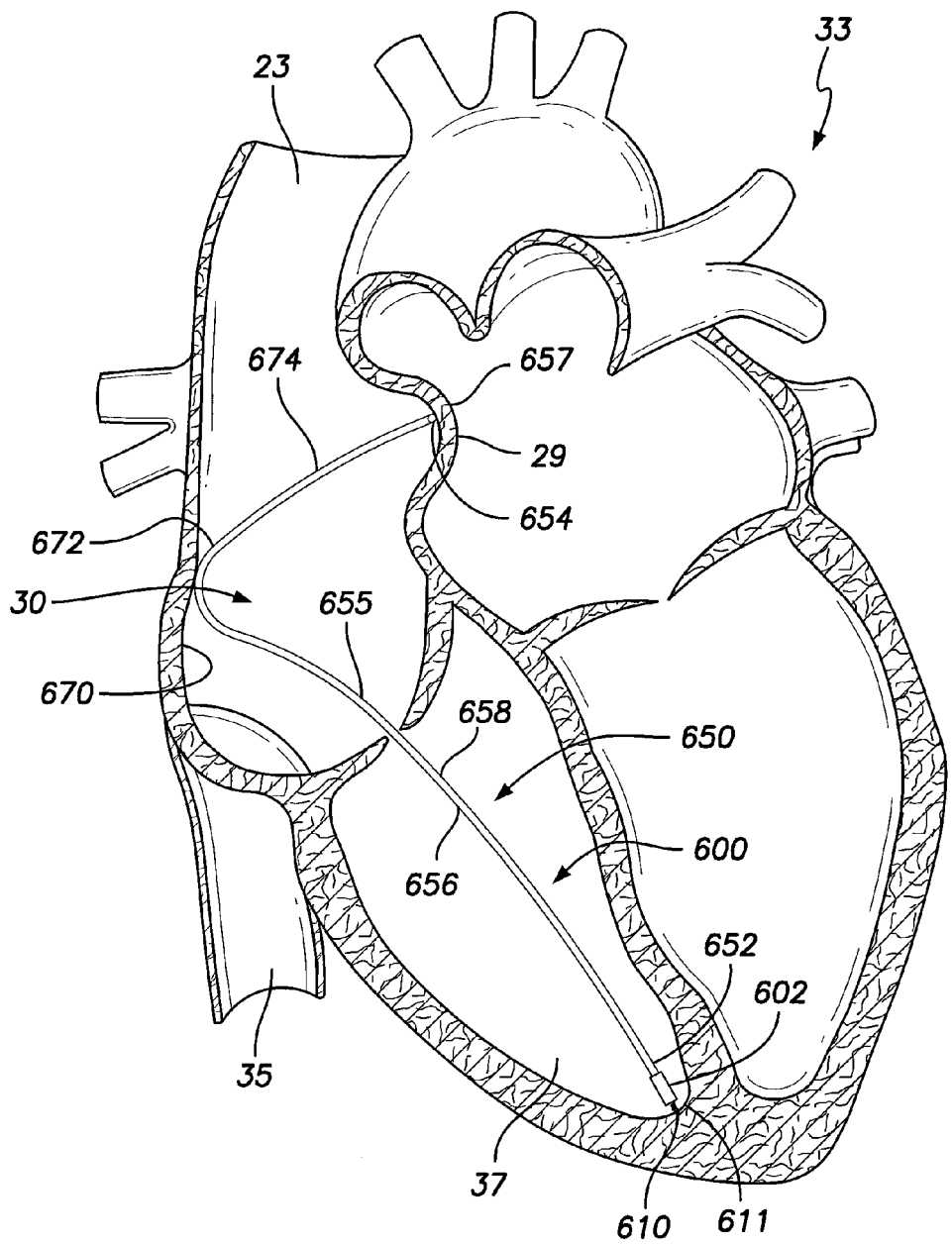
FIG. 14 illustrates a sectional view of a patient's heart having an intra-cardiac implantable medical device, according to an embodiment of the present disclosure.

FIG. 14 illustrates a sectional view of the patient's heart 33 having an intra-cardiac implantable medical device (IIMD) 600, according to an embodiment of the present disclosure. The IIMD 600 has an at-rest shape that differs from the IIMD 100 discussed above, and is configured to lodge into the heart 33 in a different manner. The IIMD 600 has been introduced and implanted through the inferior vena cava 35, through the right atrium 30 and into the right ventricle 37 of the heart 33, such as with the introducer assembly 400 described above with respect to FIG. 4, for example. Alternatively, the IIMD 600 may have been introduced through the superior vena cava 23. As another option, the IIMD 600 may be introduced into the left atrium through a pulmonary vein, into the left ventricle through the intraventricular septum, into the left ventricle through a vein, and the like.

The IIMD 600 includes a housing 602, similar to the housing 102 (shown in FIG. 1). An active fixation member 610 anchors the housing 602 to an implantation site 611, as described above.

The IIMD 600 also includes an intra-cardiac (IC) device extension 650 having a proximal end 652, a distal end 654 and an extension body 656 extending there between. The proximal end 652 may be permanently or removably (through a header style connector) coupled to the housing 602 and located in the local chamber. The extension body 656 may include an IE orientation segment 655 configured to stabilize and secure the IIMD 600 within the heart 33. A right atrial appendage (RAA) fixation mechanism 657 may be provided at the distal end 654 and abuts into, or is otherwise secured to, the right atrial appendage 29.

The extension body 656 includes a chamber transition sub-segment 658 integrally connected to the IE orientation segment 655. The IE orientation segment 655 extends into an outer wall portion 670 of the right atrium. The IE orientation segment 655, in turn, integrally connects to an arcuate curved segment 672 that inwardly curves back toward the right atrial appendage 29. The curved segment 672 integrally connects to an RAA stabilization segment 674 (including the distal end 654) that wedges between the outer wall portion 670 and the right atrial appendage 29. As such, the IIMD 100 is secured in position by way of the active fixation member 610 at the implantation site 611, the arcuate curved segment 672 abutting into the outer wall portion 670 and the RAA stabilization segment 674 abutting into the right atrial appendage 29.

The IIMD 600 may be deployed through the introducer assembly 400, as discussed above. The extension body 656 deploys toward an at-rest position, as shown in FIG. 14, as the introducer assembly 400 is removed from the IIMD 600.

The extension body 656 may be formed of a biocompatible insulated material such as EFTE, silicon, OPTIM and the like. In general, the extension body 656 may be formed of materials that are flexible yet exhibit a desired degree of shape memory such that once implanted, the RAA stabilizer segment 674, and the curved segment 672 are biased to return to a pre-formed shape. The extension body 656 may be pre-formed into a predetermined shape based upon which portion of the chamber is to be engaged.

The extension body 656 includes a flexible material having a pre-formed, memorized, permanent implanted state that is shaped to conform to select anatomical contours in the heart and to bias portions against the wall tissue at regions of interest. In an embodiment, the curved shape may be configured to follow a contour of an interior of a right atrial appendage. One curved shape may be used for all patients. As another example, prior to implant, the patient's heart may be analyzed to identify the size of one or more chambers of interest and to identify the size and/or shape of the right atrial appendage. In this example, different IC device extensions 650 may be available with different sizes and/or shapes.

Figure 15:
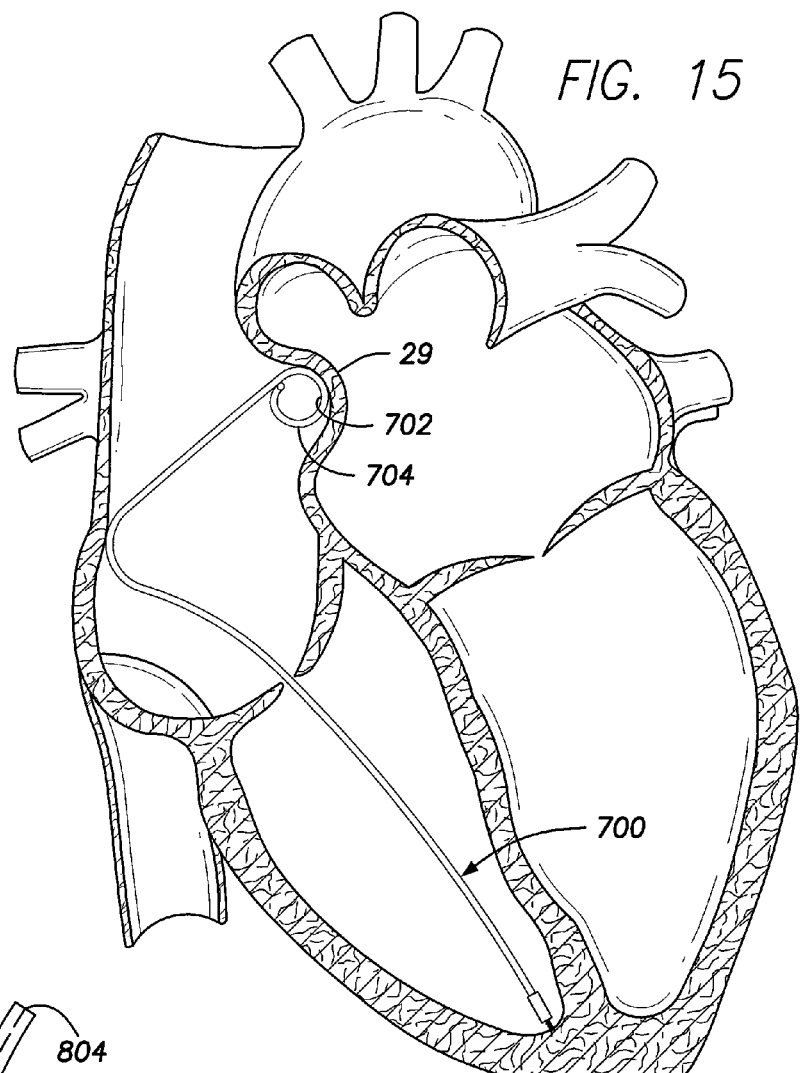
FIG. 15 illustrates a sectional view of a patient's heart having an intra-cardiac implantable medical device (IIMD), according to an embodiment of the present disclosure.

FIG. 15 illustrates a sectional view of the patient's heart 33 having an intra-cardiac implantable medical device (IIMD) 700, according to an embodiment of the present disclosure. The IIMD 700 is similar to the IIMD 700, except that the IIMD 700 includes a distal end 702 having a loop 704 that lodges into the right atrial appendage 29.

Figure 16:
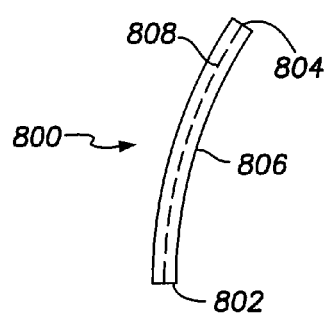
FIG. 16 illustrates a lateral view of a shape-adjusting member in an at-rest position, according to an embodiment of the present disclosure.

FIG. 16 illustrates a lateral view of a shape-adjusting member 800 in an at-rest position, according to an embodiment of the present disclosure. In this embodiment, the shape-adjusting member 800 may include a proximal end 802 connected to a distal end 804 through an intermediate curved portion 806. The intermediate curved portion 806 generally remains in an upright position, as shown in FIG. 16, and does not bend the distal end 804 back toward a longitudinal axis 808 of the shape-adjusting member 800. The shape-adjusting member 800 may be used with the introducer assembly 400 shown in FIG. 4.

In general, the shape-adjusting member 800 is sized, shaped, and formed to change the shape of a sheath of an introducer assembly in order to direct delivery of an IIMD to a desired implantation site.

Figure 17:
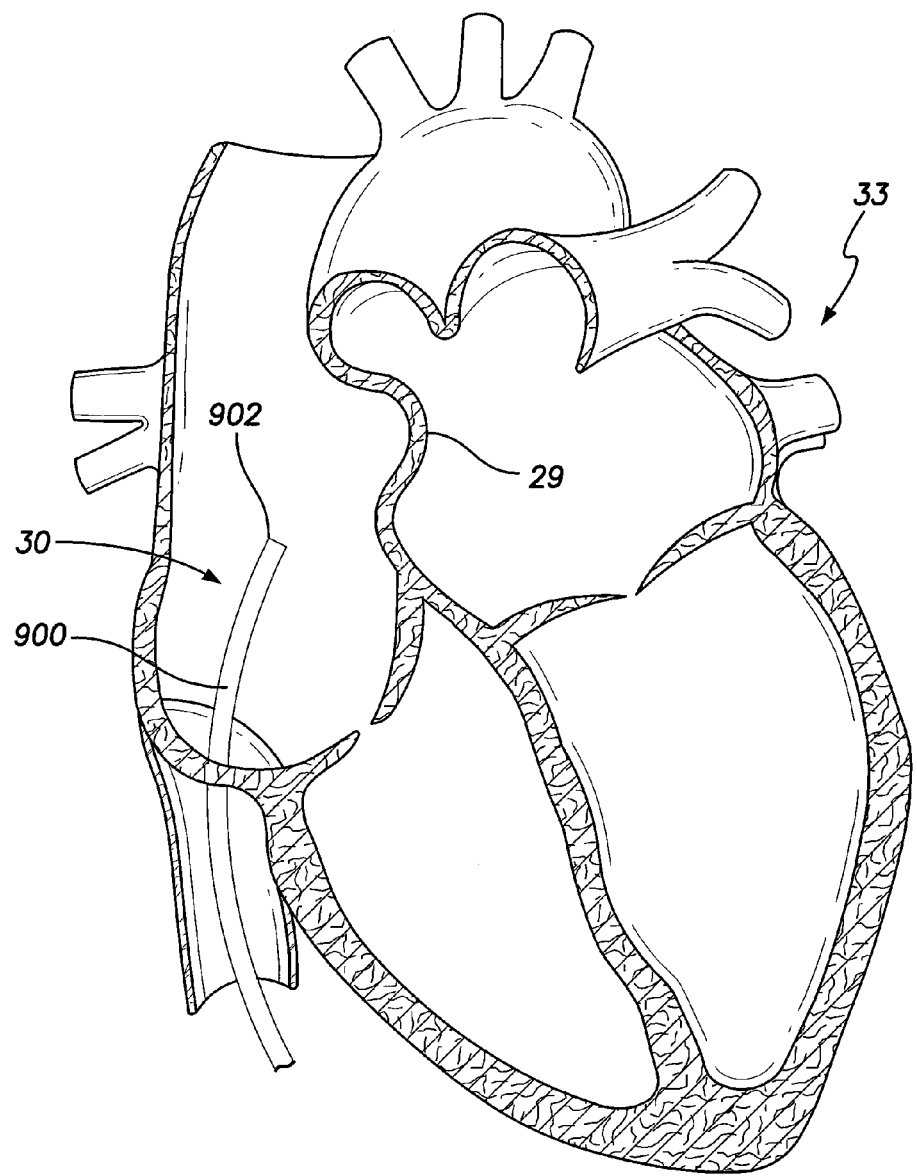
FIG. 17 illustrates a sectional view of a patient's heart with an introducer assembly moved into a right atrium, according to an embodiment of the present disclosure.

FIG. 17 illustrates a sectional view of the patient's heart 33 with an introducer assembly 900 moved into the right atrium 30, according to an embodiment of the present disclosure. The introducer assembly 900 may be similar to the introducer assembly 400 described above, except that the introducer assembly 900 may include the shape-adjusting member 800 of FIG. 16. As shown in FIG. 17, the introducer assembly 900 has been moved into the right atrium 30 through the inferior vena cava 35. The guide wire has been removed from the shape-adjusting member 800, and a distal end 902 of the introducer assembly 900 is directed toward the right atrial appendage 29. In this embodiment, the introducer assembly 900 may be operated to anchor the housing, such as housing 102, into the right atrial appendage 29. As the introducer assembly 900 is then removed from the IIMD, the memory shape of the IIMD may deploy the IIMD into various stabilizing shapes, depending on the desired at-rest position of the IIMD. For example, while the housing of the IIMD may be anchored into the right atrial appendage 29, a distal end of an extension body may deploy so that it abuts into a portion of the right ventricle, for example.

Referring to FIGS. 1-17 above, embodiments of the present disclosure provide systems for implanting an IIMD, such as through the inferior vena cava of a patient. Embodiments may be used in conjunction with surgical navigation systems, in order to accurately guide the IIMD into position. For example, the housing and distal ends of the IIMDs may include sensors, markers, fiducials, or other such components that may be tracked with an electromagnetic tracking system, for example. The surgical navigation system may be used in conjunction with a medical imaging system, such as a fluoroscopic imaging system, so that a physician may view the progress of the implantation on images generated by the imaging system.

Figure 18:
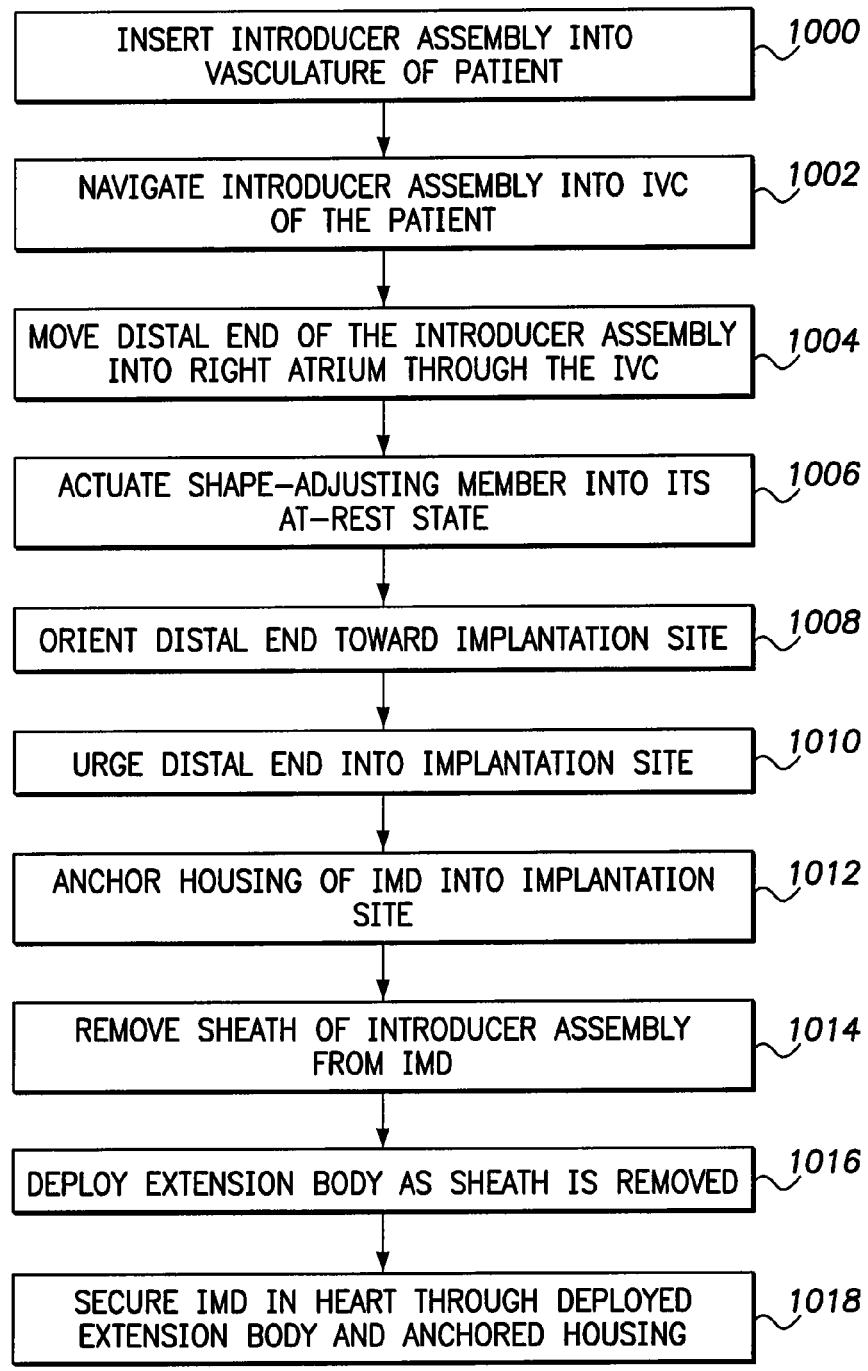
FIG. 18 illustrates a flow chart of a method of implanting an implantable medical device within a heart of a patient, according to an embodiment of the present disclosure.

FIG. 18 illustrates a flow chart of a method of implanting an intra-cardiac implantable medical device within a heart of a patient, according to an embodiment of the present disclosure. At 1000, an introducer assembly is inserted into vasculature of a patient. For example, the introducer assembly may be inserted into a femoral vein of the patient.

Next, at 1002, the introducer assembly is navigated through the vasculature and passes into the inferior vena cava of the heart of the patient. Then, at 1004, a distal end of the introducer assembly is moved into the right atrium.

At 1006, a shape-adjusting member of the introducer assembly is actuated into an at-rest state. For example, a stiffening guide wire may be removed from the shape-adjusting member. Optionally, wires connected to the shape-adjusting member may be tightened or loosened to change the shape of the shape-adjusting member. The shape-adjusting member is actuated in order to change the shape of a portion of the introducer assembly, so that the distal end is oriented toward an implantation site, such as a ventricular apex, at 1008. The sheath is then slid over the shape-adjusting member so that the distal end of the sheath is directed toward the implantation site. Then, at 1010, the distal end is urged into the implantation site. At 1012, a housing of an IIMD is anchored into the implantation site.

After the housing of the IIMD is anchored into the implantation site, a sheath of the introducer assembly is removed from the IIMD at 1014. At 1016, as the sheath continues to be removed, an extension body, through shape memory, deploys within the heart. The extension body may have an at-rest shape that is configured to deploy to desired locations within the heart. Finally, at 1018, the IIMD is secured in the heart through the deployed extension body and the anchored housing. For example, the IIMD may be secured within the heart at three different locations: the implantation site, proximate the right atrial appendage, and proximate an opening of the inferior vena cava.

Figure 19:
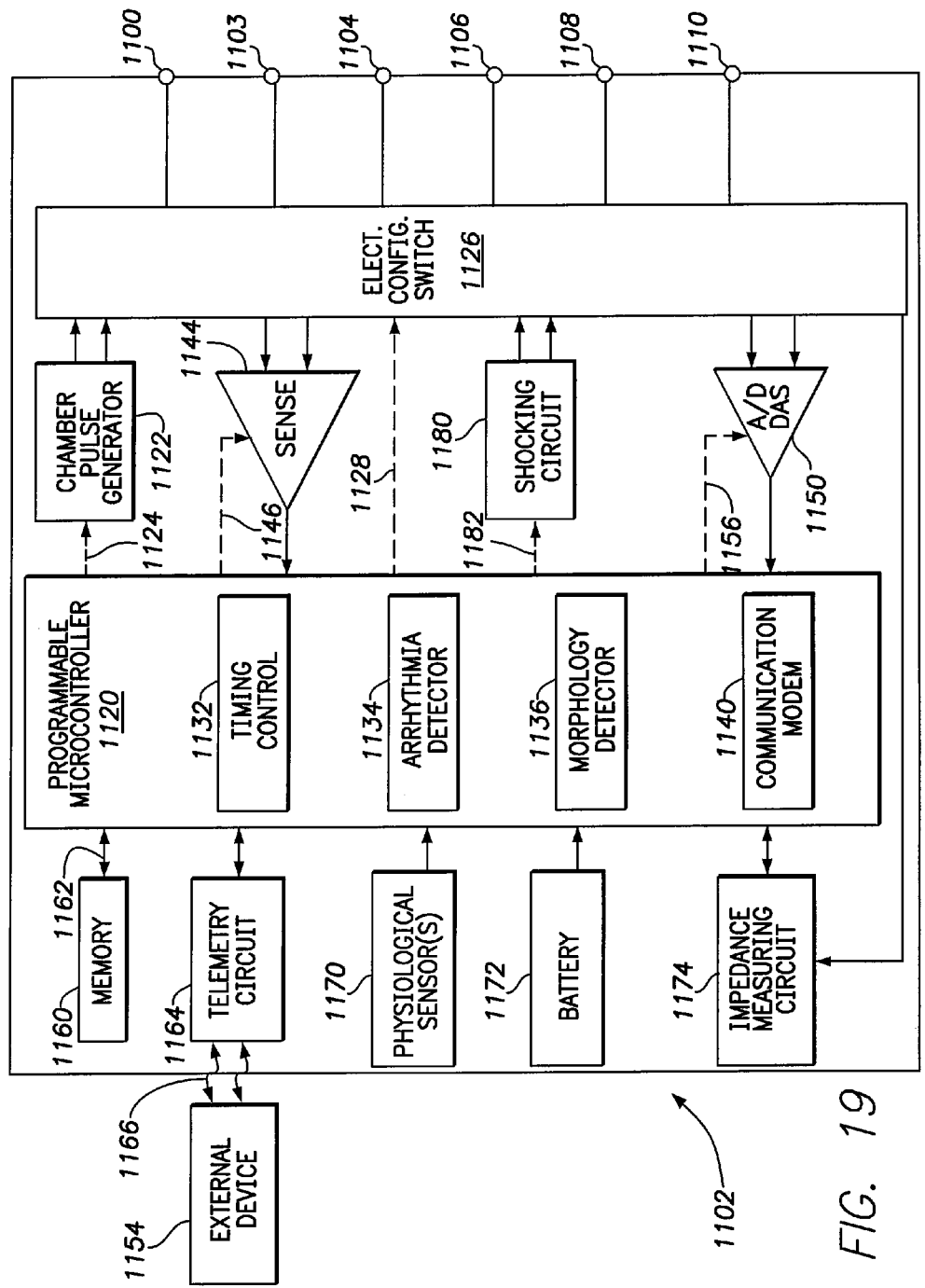
FIG. 19 illustrates an exemplary block diagram of the electrical components of an implantable medical device, according to an embodiment of the present disclosure.

FIG. 19 illustrates an exemplary block diagram of the electrical components of an IIMD 1102, according to an embodiment of the present disclosure. The IIMD 1102 may be implemented as a full-function biventricular pacemaker, equipped with both atrial and ventricular sensing and pacing circuitry for four chamber sensing and stimulation therapy (including both pacing and shock treatment). Optionally, the IIMD 1102 may provide full-function cardiac resynchronization therapy. Alternatively, the IIMD 1102 may be implemented with a reduced set of functions and components. For instance, the IIMD 1102 may be implemented without ventricular sensing and pacing.

The IIMD 1102 includes a housing 1100 that securely contains the electronic/computing components. The housing 1100 (which is often referred to as the "can", "case", "encasing", or "case electrode") may be programmably selected to act as the return electrode for certain stimulus modes. The housing 1100 further includes a connector (not shown) with a plurality of terminals 1103, 1104, 1106, 1108, and 1110. The terminals may be connected to electrodes that are located in various locations within and about the heart. For example, the terminals may include: a terminal 1103 to be coupled to a first electrode (e.g. a tip electrode) located in a first chamber; a terminal 1104 to be coupled to a second electrode (e.g., tip electrode) located in a second chamber; a terminal 1106 to be coupled to an electrode (e.g. ring) located in the first chamber; a terminal 1108 to be coupled to an electrode located (e.g. ring electrode) in the second chamber; and a terminal 1110 to be coupled to an electrode (e.g., coil) located in the SVC. The type and location of each electrode may vary. For example, the electrodes may include various combinations of ring, tip, coil and shocking electrodes and the like.

The IIMD 1102 includes a programmable microcontroller 1120 that controls various operations of the IIMD 1102, including cardiac monitoring and stimulation therapy. Microcontroller 1120 includes a microprocessor (or equivalent control circuitry), RAM and/or ROM memory, logic and timing circuitry, state machine circuitry, and I/O circuitry.

IIMD 1102 further includes a first chamber pulse generator 1122 that generates stimulation pulses for delivery by one or more electrodes coupled thereto. The pulse generator 1122 is controlled by the microcontroller 1120 via control signal 1124. The pulse generator 1122 is coupled to the select electrode(s) via an electrode configuration switch 1126, which includes multiple switches for connecting the desired electrodes to the appropriate I/O circuits, thereby facilitating electrode programmability. The switch 1126 is controlled by a control signal 1128 from the microcontroller 1120.

In the example of FIG. 19, a single pulse generator 1122 is illustrated. Optionally, the IIMD 1102 may include multiple pulse generators, similar to pulse generator 1122, where each pulse generator is coupled to one or more electrodes and controlled by the microcontroller 1120 to deliver select stimulus pulse(s) to the corresponding one or more electrodes.

Microcontroller 1120 is illustrated as including timing control circuitry 1132 to control the timing of the stimulation pulses (e.g., pacing rate, atrio-ventricular (AV) delay, atrial interconduction (A-A) delay, or ventricular interconduction (V-V) delay, etc.). The timing control circuitry 1132 may also be used for the timing of refractory periods, blanking intervals, noise detection windows, evoked response windows, alert intervals, marker channel timing, and so on. Microcontroller 1120 also has, an arrhythmia detector 1134 for detecting arrhythmia conditions and a morphology detector 1136. Although not shown, the microcontroller 1120 may further include other dedicated circuitry and/or firmware/software components that assist in monitoring various conditions of the patient's heart and managing pacing therapies.

The IIMD 1102 is further equipped with a communication modem (modulator/demodulator) 1140 to enable wireless communication with the remote slave pacing unit 1106. In one implementation, the communication modem 1140 uses high frequency modulation. As one example, the modem 1140 transmits signals between a pair of electrodes of the lead assembly 1104, such as between the can 1100 and the right ventricular tip electrode 1122. The signals are transmitted in a high frequency range of approximately 20-80 kHz, as such signals travel through the body tissue in fluids without stimulating the heart or being felt by the patient.

The communication modem 1140 may be implemented in hardware as part of the microcontroller 1120, or as software/firmware instructions programmed into and executed by the microcontroller 1120. Alternatively, the modem 1140 may reside separately from the microcontroller as a standalone component.

The IIMD 1102 includes sensing circuitry 1144 selectively coupled to one or more electrodes that perform sensing operations, through the switch 1126 to detect the presence of cardiac activity in the corresponding chambers of the heart. The sensing circuit 1144 is configured to perform bipolar sensing between one pair of electrodes and/or between multiple pairs of electrodes. The sensing circuit 1144 detects NF electrical activity and rejects FF electrical activity. The sensing circuitry 1144 may include dedicated sense amplifiers, multiplexed amplifiers, or shared amplifiers. The sensing circuitry 1144 may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 1126 determines the sensing polarity of the cardiac signal by selectively closing the appropriate switches. In this way, the clinician may program the sensing polarity independent of the stimulation polarity.

The output of the sensing circuitry 1144 is connected to the microcontroller 1120 which, in turn, triggers or inhibits the pulse generator 1122 in response to the absence or presence of cardiac activity. The sensing circuitry 1144 receives a control signal 1146 from the microcontroller 1120 for purposes of controlling the gain, threshold, polarization charge removal circuitry (not shown), and the timing of any blocking circuitry (not shown) coupled to the inputs of the sensing circuitry.

In the example of FIG. 19, a single sensing circuit 1144 is illustrated. Optionally, the IIMD 1102 may include multiple sensing circuits, similar to sensing circuit 1144, where each sensing circuit is coupled to one or more electrodes and controlled by the microcontroller 1120 to sense electrical activity detected at the corresponding one or more electrodes. The sensing circuit 1144 may operate in a unipolar sensing configuration or in a bipolar sensing configuration.

The IIMD 1102 further includes an analog-to-digital (ND) data acquisition system (DAS) 1150 coupled to one or more electrodes via the switch 1126 to sample cardiac signals across any pair of desired electrodes. The data acquisition system 1150 is configured to acquire intracardiac electrogram signals, convert the raw analog data into digital data, and store the digital data for later processing and/or telemetric transmission to an external device 1154 (e.g., a programmer, local transceiver, or a diagnostic system analyzer). The data acquisition system 1150 is controlled by a control signal 1156 from the microcontroller 1120.

The microcontroller 1120 is coupled to a memory 1160 by a suitable data/address bus 1162. The programmable operating parameters used by the microcontroller 1120 are stored in memory 1160 and used to customize the operation of the IIMD 1102 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of the IIMD 1102 may be non-invasively programmed into the memory 1160 through a telemetry circuit 1164 in telemetric communication via communication link 1166 with an external device 1154. The telemetry circuit 1164 allows intracardiac electrograms and status information relating to the operation of the IIMD 1102 (as contained in the microcontroller 1120 or memory 1160) to be sent to the external device 1154 through the established communication link 1166.

The IIMD 1102 can further include magnet detection circuitry (not shown), coupled to the microcontroller 1120, to detect when a magnet is placed over the unit. A magnet may be used by a clinician to perform various test functions of the unit 1102 and/or to signal the microcontroller 1120 that the external programmer 1154 is in place to receive or transmit data to the microcontroller 1120 through the telemetry circuit 1164.

The IIMD 1102 can further include one or more physiologic sensors 1170. Such sensors are commonly referred to as "rate-responsive" sensors because they are typically used to adjust pacing stimulation rates according to the exercise state of the patient. However, the physiological sensor 1170 may further be used to detect changes in cardiac output, changes in the physiological condition of the heart, or diurnal changes in activity (e.g., detecting sleep and wake states). Signals generated by the physiological sensors 1170 are passed to the microcontroller 1120 for analysis. The microcontroller 1120 responds by adjusting the various pacing parameters (such as rate, AV Delay, V-V Delay, etc.) at which the atrial and ventricular pacing pulses are administered. While shown as being included within the unit 1102, the physiologic sensor(s) 1170 may be external to the unit 1102, yet still be implanted within or carried by the patient. Examples of physiologic sensors might include sensors that, for example, sense respiration rate, pH of blood, ventricular gradient, activity, position/posture, minute ventilation (MV), and so forth.

A battery 1172 provides operating power to all of the components in the IIMD 1102. The battery 1172 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 1172 also desirably has a predictable discharge characteristic so that elective replacement time can be detected. As one example, the IIMD 1102 employs lithium/silver vanadium oxide batteries.

The IIMD 1102 may also include an impedance measuring circuit 1174, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 1174 is coupled to the switch 1126 so that any desired electrode may be used. The microcontroller 1120 further controls a shocking circuit 1180 by way of a control signal 1182. The shocking circuit 1180 generates shocking pulses of low (e.g., up to 0.5 joules), moderate (e.g., 0.5-10 joules), or high energy (e.g., 611 to 40 joules), as controlled by the microcontroller 1120.

Referring to FIGS. 1-19, embodiments of the present disclosure provide systems and methods for delivering an IIMD into the heart of a patient through the inferior vena cava, for example. Embodiments provide systems and methods that are well-suited for inferior vena cava delivery. Moreover, embodiments provide systems and methods for implanting an IIMD that are cost-effective and intuitive.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. An intra-cardiac implantable medical device (IIMD) system, comprising:
 a housing configured to be implanted entirely within a local chamber of the heart, wherein the housing includes a base configured to be secured to the local chamber; and
 an intra-cardiac (IC) device extension including a proximal end, a distal end, and an extension body extending there between, the proximal end coupled to the housing and configured to be located in the local chamber, the extension body including an IIMD-to-electrode (IE) orientation segment connected to a chamber transition segment that is sufficient in length to extend from the local chamber into an adjacent chamber proximate an inferior vena cava, wherein at least a portion of the IE orientation segment is configured to be lodged within the adjacent chamber proximate the inferior vena cava in order to stabilize the system within heart.

2. The system of claim 1, wherein the housing is configured to be securely anchored within the local chamber, and the IC device extension is configured to be securely lodged between wall portions of the adjacent chamber.

3. The system of claim 1, wherein the IE orientation segment comprises a right atrial appendage (RAA) stabilization segment connected to an inferior vena cava (IVC) stabilization segment through a spanning segment, wherein the RAA stabilization segment is configured to be proximate an RAA of the heart and the IVC stabilization segment is configured to be proximate the inferior vena cava of the heart.

4. The system of claim 3, wherein the RAA stabilization segment comprises an RAA fixation mechanism having at least one electrode configured to abut into a portion of the RAA.

5. An intra-cardiac implantation system comprising:
 an intra-cardiac implantable medical device (IIMD) configured to be implanted into a heart, the IIMD including:
  a housing configured to be implanted entirely within a local chamber of the heart, wherein the housing includes a base configured to be secured to the local chamber; and
  an intra-cardiac (IC) device extension including an extension proximal end, an extension distal end, and an extension body extending there between, the extension body including a IIMD-to-electrode (IE) orientation segment connected to a chamber transition segment that is sufficient in length to extend from the local chamber into an adjacent chamber; and
 an introducer assembly configured to implant the IIMD into the heart, the introducer assembly comprising:
  a sheath having a sheath proximal end and a sheath distal end, wherein an internal passage is defined between the sheath proximal and distal ends, wherein the housing and the IC device extension are configured to be moved through the sheath distal end, and wherein the IC device extension is in a collapsed state while in the sheath; and
  a shape-adjusting member positioned within or over a portion of the sheath, wherein the shape-adjusting member is configured to be selectively transitioned between a navigation state, in which the sheath is configured to be navigated through vasculature of the patient, and an at-rest state, in which the sheath distal end is configured to be directed toward an implantation site within the heart.

6. The system of claim 5, wherein the introducer assembly further comprises a guide member operatively connected to the shape-adjusting member, wherein the guide member is configured to selectively transition the shape-adjusting member between the navigation and at-rest states.

7. The system of claim 6, wherein the guide member comprises one or both of a guide wire or guide tube.

8. The system of claim 7, wherein the one or both of a guide wire or guide tube are positioned within a central passage of the shape-adjusting member.

9. The system of claim 5, wherein the introducer assembly further comprises a removal wire connected to the shape-adjusting member, wherein the removal wire is configured to remove the shape-adjusting member from the sheath.

10. The system of claim 5, wherein the introducer assembly is configured to implant the IIMD into the heart such that the housing is located in the local chamber, and the IE orientation segment is lodged within the adjacent chamber in order to stabilize the IIMD within heart.

11. The system of claim 5, wherein the introducer assembly is configured to implant the IIMD into the heart such that the housing is securely anchored within the local chamber, and the IC device extension is securely lodged between wall portions of the adjacent chamber.

12. The system of claim 5, wherein the IE orientation segment comprises a right atrial appendage (RAA) stabilization segment connected to an inferior vena cava (IVC) stabilization segment through a spanning segment.

13. The system of claim 12, wherein the introducer assembly is configured to implant the IIMD into the heart so that the RAA stabilization segment is proximate an RAA of the heart and the IVC stabilization segment is proximate an IVC of the heart.

14. The system of claim 13, wherein the RAA stabilization segment comprises an RAA fixation mechanism having at least one electrode configured to abut into a portion of the RAA.

15. The system of claim 13, wherein the RAA stabilization segment comprises the distal end configured to abut into the RAA, and wherein the IVC stabilization segment comprises an arcuate curved segment configured to abut into a wall portion of the right atrium opposite the RAA.

16. An intra-cardiac implantation method configured to implant an intra-cardiac implantable medical device (IIMD) into a heart, wherein the IIMD includes a housing configured to be implanted entirely within a local chamber of the heart, and an intra-cardiac (IC) device extension including a proximal end, a distal end, and an extension body extending therebetween, wherein the extension body includes an IE orientation segment connected to a chamber transition segment that is sufficient in length to extend from the local chamber into an adjacent chamber, the method comprising:

navigating an introducer assembly having a sheath through vasculature;

adjusting a shape of the introducer assembly with a shape-adjusting member within the adjacent chamber so that a sheath distal end of the introducer assembly is directed toward an implantation site;

holding the shape-adjusting member in position within the sheath;

sliding the sheath over the shape-adjusting member;

urging the sheath distal end into the implantation site;

pushing the housing of the IIMD through the sheath distal end into the implantation site;

anchoring the housing into the implantation site;

removing the sheath from the IIMD;

deploying the extension body within the heart during the removing operation; and stabilizing the IIMD within the heart through the anchoring and deploying operations.

17. The method of claim 16, further comprising initially positioning the housing and the IC device extension within the sheath distal end of the introducer assembly before the navigating operation, wherein the positioning operation comprises collapsing the IC device extension within the sheath distal end.

18. The method of claim 16, wherein the adjusting operation comprises curving the shape-adjusting member so that the sheath distal end is directed toward an implantation site within the local chamber.

19. The method of claim 16, wherein the adjusting operation comprises transitioning the shape-adjusting member from a navigation state to an at-rest state.

20. The method of claim 19, wherein the adjusting operation comprises transitioning the shape-adjusting member from the navigation state to the at-rest state through a guide member.

21. The method of claim 16, further comprising removing the shape-adjusting member from the sheath after the adjusting operation.

22. The method of claim 16, wherein the anchoring operation comprises anchoring the housing in the local chamber.

23. The method of claim 22, wherein the securing operation comprises lodging the IE orientation segment within the adjacent chamber in order to stabilize the IIMD within heart.

24. The method of claim 22, wherein the securing operation comprises lodging the IC device between wall portions of the adjacent chamber.

25. The method of claim 16, wherein the stabilizing operation comprises positioning an RAA stabilization segment of the IE orientation segment proximate a right atrial appendage of the heart, and positioning an IVC stabilization segment of the IE orientation segment proximate an inferior vena cava of the heart.

* * * * *